United States Patent [19]

Sciavolino

[11] 4,180,654

[45] Dec. 25, 1979

[54] 4"-DEOXY-4"-ACYLAMIDO DERIVATIVES OF OLEANDOMYCIN, ERYTHROMYCIN AND ERYTHROMYCIN CARBONATE

[75] Inventor: Frank C. Sciavolino, East Lyme, Conn.

[73] Assignee: Pfizer Inc., New York, N.Y.

[21] Appl. No.: 937,640

[22] Filed: Aug. 29, 1978

Related U.S. Application Data

[63] Continuation-in-part of Ser. No. 866,722, Jan. 3, 1978, abandoned.

[51] Int. Cl.² ............................................. C07H 17/08
[52] U.S. Cl. ..................................... 536/9; 536/17 R; 424/180
[58] Field of Search ....................................... 536/9, 17

[56] References Cited

U.S. PATENT DOCUMENTS

| | | | |
|---|---|---|---|
| 3,869,445 | 3/1975 | Hallas et al. | 536/9 |
| 3,884,902 | 5/1975 | Hallas et al. | 536/9 |
| 3,884,903 | 5/1975 | Jones et al. | 536/9 |
| 4,063,014 | 12/1977 | Hallas et al. | 536/9 |
| 4,069,379 | 1/1978 | Sciavolino | 536/9 |
| 4,085,119 | 4/1978 | Myers | 536/9 |

*Primary Examiner*—Johnnie R. Brown
*Assistant Examiner*—Blondel Hazel
*Attorney, Agent, or Firm*—Francis X. Murphy; Charles J. Knuth; Albert E. Frost

[57] ABSTRACT

Derivatives of oleandomycin, erythromycin A and B, erythromycylamine and erythromycin carbonate, having at the 4"-position an acylamido group, their preparation and use as antibacterial agents are described.

41 Claims, No Drawings

4"-DEOXY-4"-ACYLAMIDO DERIVATIVES OF OLEANDOMYCIN, ERYTHROMYCIN AND ERYTHROMYCIN CARBONATE

CROSS-REFERENCE TO RELATED APPLICATIONS

This application is a continuation-in-part of copending application Ser. No. 866,722, filed Jan. 3, 1978, now abandoned.

BACKGROUND OF THE INVENTION

1. Field of the Invention

This invention relates to semisynthetic macrolides, and, more particularly, to 4"-deoxy-4"-acylamido derivatives of oleandomycin, its 11- and 2'-monoalkanoyl and 11,2'-dialkanoyl esters, erythromycin A, its 11- and 2'-monoalkanoyl and 11,2'-dialkanoyl esters, and 6,9-hemiketal derivatives, erythromycin B and its 2'-monoalkanoyl ester, erythromycin A carbonate and its 2'-monoalkanoyl esters and 6,9-hemiketal derivatives, and erythromycylamine, to methods for their preparation and to their use as antibacterial agents.

2. Description of the Prior Art

Oleandomycin and erythromycin are macrolide antibiotics produced by fermentation and described in U.S. Pat. Nos. 2,757,123 and 2,653,899, respectively. Numerous derivatives of oleandomycin and of erythromycins A and B have been prepared in efforts to modify their biological and/or pharmacodynamic properties.

Derivatization of oleandomycin has focused primarily upon the formation of esters at one or more of the hydroxy groups located at the 2'-, 4"- and 11-positions. Mono-, di- and triacyl esters wherein the acyl moiety is derived from a lower aliphatic hydrocarbon monocarboxylic acid having from 2 to 6 carbon atoms are described in U.S. Pat. No. 3,022,219. Aminohydrin derivatives of oleandomycin are reported by Kastons, et al., *Khim. Geterosikl. Soedin* (2) 168-71 (1974); C.A. 80, 145986n (1974). The compounds, for which no utility is reported, are prepared by treating oleandomycin with a dialkylamine or a heterocyclic amine in a sealed tube for 20 hours at 30° C. The epoxide moiety at the 8-position is the site of reaction.

Various monoesters and cyclic anhydrides of erythromycin are reported in *Antibiotics Annual*, 1953-1954, Proc. Symposium Antibiotics (Washington, D.C.), pages 500-513 and 514-521, respectively. U.S. Pat. No. 3,417,077 describes the cyclic carbonate ester of erythromycin A, the reaction product of erythromycin A and ethylene carbonate, as an active antibacterial agent. U.S. Pat. No. 3,884,903 discloses 4"-deoxy-4"-oxo-erythromycin A and B derivatives as useful antibiotics.

The 9-amino derivative of erythromycin A, known as erythromycylamine, has been extensively investigated and derivatized. Sulfonamide derivatives of erythromycylamine are described in U.S. Pat. No. 3,983,103 as antibacterial agents. N-alkyl derivatives of erythromycylamine are reported by Ryden, et al., *J. Med. Chem.*, 16, 1059 (1973) to have in vitro and in vivo antibacterial activity.

SUMMARY OF THE INVENTION

It has now been found that certain acyl derivatives of 4"-deoxy-4"-amino derivatives of oleandomycin, erythromycin A and B, erythromycin carbonate and erythromycylamine exhibit valuable antibacterial activity in vitro as well as in vivo via the parenteral and oral routes of administration, particularly against Gram-positive microorganisms. Many of the compounds described herein also exhibit activity against Gram-negative microorganisms. The compounds of this invention have formulae I-IV below wherein the wavy line connecting the acylamino group at the 4"-position is generic to and embracive of both epimeric forms:

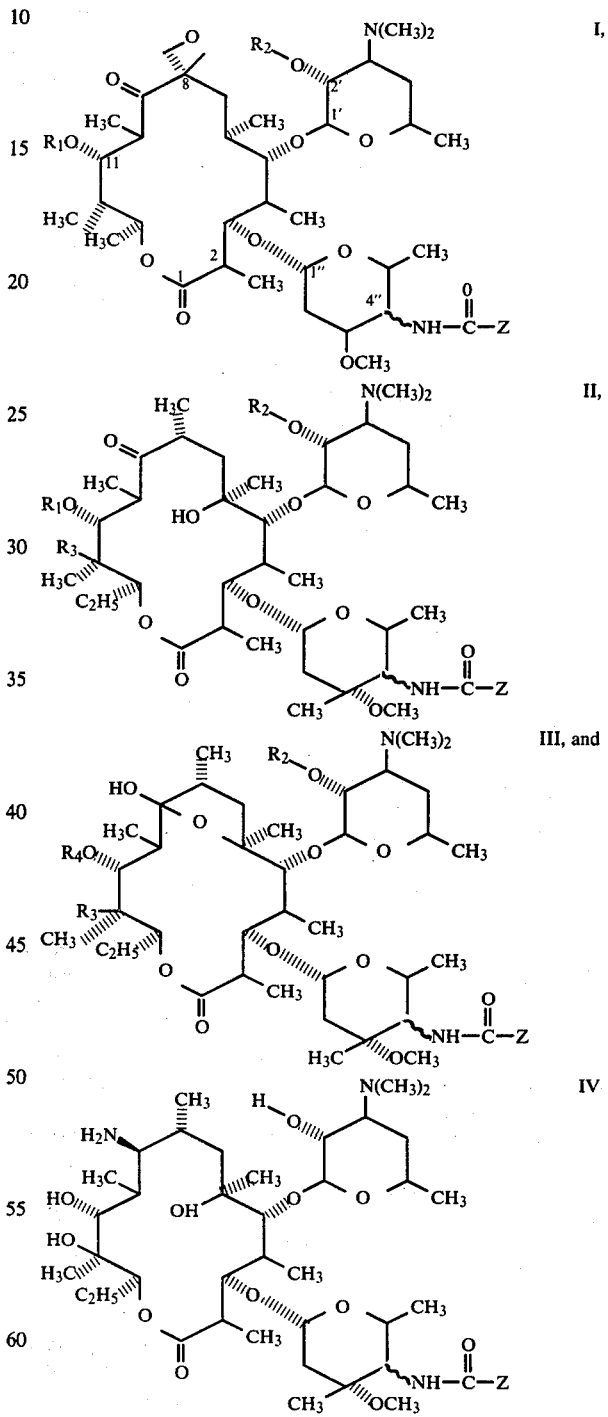

wherein each of $R_1$ and $R_2$ is selected from the group consisting of hydrogen and alkanoyl having from two to three carbon atoms; $R_3$ is selected from the group consisting of hydrogen and hydroxy; $R_4$ is alkanoyl having from two to three carbon atoms; $R_4O$ and $R_3$ when taken together are $$-O-\overset{\overset{\displaystyle O}{\|}}{C}-O-;$$

$R_1O$ and $R_3$ when taken together are $$-O-\overset{\overset{\displaystyle O}{\|}}{C}-O-;$$

Z is selected from the group consisting of
(a) $-(CH_2)_m-C(CH_3)_3$;

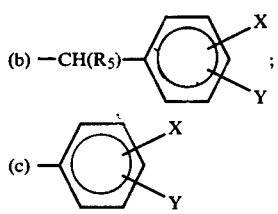

(d) $-(CH_2)_m$-heterocyclyl;
m is 0 or 1;

$R_5$ is selected from the group consisting of hydrogen, chloro, hydroxy, methyl, amino and alkoxy having from one to four carbon atoms;

X is selected from the group consisting of hydrogen, chloro, bromo, fluoro, alkyl having from one to four carbon atoms, alkoxy having from one to four carbon atoms;

Y is selected from the group consisting of X, trifluoromethyl and carbalkoxy having from two to five carbon atoms; and heterocyclyl is selected from the group consisting of thienyl, pyrazinyl, pyridyl, furyl, imidazolyl, thiazolyl, isothiazolyl, oxazolyl, isoxazolyl, thiadiazolyl, pyrrolyl, and monomethyl derivatives of said heterocyclyls.

Compounds of the above formulae, including the epimeric forms thereof, and their pharmaceutically acceptable salts are effective antibacterial agents against Gram-positive microorganisms, e.g. *Stephylococcus aureus* and *Streptococcus pyogenes*, in vitro and many are active in vivo via the parenteral and oral routes of administration. Many of the compounds (and their salts) are also active against certain Gram-negative microorganisms, such as cocci, e.g., *Pasteurella multocida* and *Neisseria sicca*.

Favored compounds of this invention because of their relatively greater activity and potency are those having the values tabulated below wherein all Z values apply to formulae I-IV:

| Formula | $R_2$ | $R_1$ | $R_3$ | $OR_4$ | Z |
|---|---|---|---|---|---|
| I | H | H or $COCH_3$ | — | — | (a) $-(CH_2)_m-C(CH_3)_3$; m = 0, 1; |
| II | H | H or $COCH_3$ | H | — | (b) $CH(R_5)$-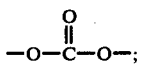 where $R_5$ = H, Cl, or $OCH_3$ |
| | | | $-O-C(O)-O-$ | — | |
| III | H | | $-O-C(O)-O-$ | | (c) 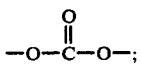 |
| IV | — | [9 (S)—$NH_2$] | — | — | (d) $-(CH_2)_m$-heterocyclyl; m = 0 |

Preferred compounds of this invention are those favored compounds wherein Z is $-C(CH_3)_3$,

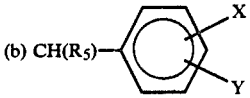, 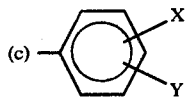

wherein Y is hydrogen, chloro or fluoro; 2-pyrazinyl, 4-methyl-5-thiazolyl, 4-methyl-5-oxazolyl and isoxazolyl.

Especially preferred are those preferred compounds wherein Z is one of the above-mentioned heterocyclyl groups and $R_1$ is hydrogen.

DETAILED DESCRIPTION OF THE INVENTION

Compounds having formulae I-III above are prepared by acylation of the corresponding 4"-amino derivative with the appropriate acylating agent. The acylation reaction is carried out by contacting the appropriate 4"-amino derivative in a reaction-inert solvent with a reactive derivative of the appropriate acylating agent. Typical reactive derivatives of the acylating agents are the acid chlorides, anhydrides (simple or mixed), acid azide, an active ester or thioester with, for example, N-hydroxyphthalimide, N-hydroxysuccinimide, a phenol or thiophenol, and the "condensation product" with a "condensing" agent such as a carbodiimide, an alkoxyacetylene, N,N'-carbonyldiimidazole, N,N'-carbonylditriazole and hexahalocyclotriphosphatriazines.

The preferred acylation process of this invention comprises reaction of the appropriate 4"-amino precursor of formulae I-III compounds with the acid chloride (or bromide) of the appropriate acylating agent in the presence of an acid acceptor. Suitable acid acceptors are tertiary amines such as trialkylamines having from 1-4 carbon atoms per alkyl group, N-methylaniline, pyridine, N-ethylpiperidine and N-methylmorpholine. When an aqueous system is used as solvent, an inorganic base such as an alkali metal hydroxide, can be used as acid acceptor. The acylation can be conducted in aqueous or nonaqueous solvent systems. In aqueous systems, the reaction is generally carried out at a pH of from about 6 to about 9 and at a temperature of from about 0° C. to about 50° C. It can also be performed in unstable emulsions of water and water-immiscible organic solvents such as methyl isobutyl ketone and lower alkyl acetates over the pH range of from about 2 to about 4. In non-aqueous systems the reaction is carried out at from about 0° C. to about 50° C. in the presence of a solvent soluble acid acceptor such as a tertiary amine as enumerated above.

Also preferred is the reaction of the appropriate 4"-amino compound with the acid form of the appropriate acylating agent in the presence of a carbodiimide. This process is frequently preferred for reasons of convenience, availability of reactants and overall yield of product. When using a carbodiimide as condensing agent, aqueous or non-aqueous solvent systems can be used. When an aqueous system is used, pH is desirably adjusted to the range of about 5 to about 8, and preferably to about 6 to about 7. In a typical procedure, the acid reactant and carbodiimide are mixed in equimolar proportions in a suitable solvent (tetrahydrofuran, dioxane), and a solution of water and a water miscible organic solvent (water plus dioxane or tetrahydrofuran) containing the aminoacrolide reactant is added at room temperature. The mixture is stirred for several hours until reaction is complete. Temperatures of from about −5° C. to about 30° C. are generally used. In most instances, an excess of up to about 10% of the condensing agent is used. The acylated product is recovered by methods known in the art.

Compounds of formula IV are conveniently prepared from compounds of formula II ($R_1$=H, $R_3$=OH) by converting the 9-oxo group of formula II compounds to the corresponding 9-hydrazone followed by reaction of the hydrazone with nitrous acid. The 9-imino derivative thus produced is reduced to the 9-amino derivative by sodium borohydride. The process comprises reacting the appropriate formula II compound with excess anhydrous hydrazine in an appropriate solvent such as an alcohol having from one to four carbon atoms at a temperature of from about 0° C. to about 100° C. The product is isolated by evaporation under reduced pressure to remove solvent and excess hydrazine. The 9-hydrazone derivative is converted to the 9-imino derivative by treatment in a suitable solvent, e.g. an alcohol having from one to four carbon atoms, with sodium nitrite at pH of about 4 to 5 and a temperature of from about 0° C. to about 10° C. The imine can be isolated by known methods if desired or can be reduced in situ to the desired 9-amino compound by treatment with sodium borohydride at a pH of about 8. The products of formula IV are isolated by known methods as described herein. This procedure affords the favored 9(S)-epimer.

Alternatively, formula IV compounds are prepared by conversion of formula II ($R_1$=H, $R_3$=OH) compounds to the corresponding 9-oxime by reaction with hydroxylamine in dry methanol at from about 0° C. to about 50° C. The oxime is reduced using excess Raney nickel or catalytically over $PtO_2$ in glacial acetic acid at 700-1000 psi hydrogen pressure for periods of 12-18 hours. Raney nickel reduction affords the 9(R)-epimer as predominant product whereas $PtO_2/H_2$ affords the 9(S)-epimer as principal product. Since the above reduction methods afford mixtures of the 9(S)- and 9(R)-epimers, conversion of the hydrazone to the 9-imine and $NaBH_4$ reduction of the imine is the favored process for producing compounds of formula IV.

A further alternative comprises conversion of the 9-oxime of formula II compounds to the 9-imine by treatment with titanium trichloride followed by $NaBH_4$ reduction of the imine as described above.

Acid addition salts of the compounds of this invention are readily prepared by treating compounds having formulae I–IV with at least an equimolar amount of the appropriate acid in a reaction-inert solvent. When more than one basic group is present in a compound of formulae I–IV, the addition of sufficient acid to satisfy each basic group permits formation of polyacid addition salts. The acid addition salts are recovered by filtration if they are insoluble in the reaction-inert solvent, by precipitation by addition of a non-solvent for the acid-addition salt, or by evaporation of the solvent. Representative of such salts, but not limited thereto, are the hydrochloride, hydrobromide, phosphate, sulfate, formate, acetate, propionate, butyrate, citrate, glycolate, lactate, tartrate, malate, maleate, fumarate, gluconate, stearate, mandelate, pamoate, benzoate, succinate, lactate, p-toluenesulfonate and aspartate.

The 11-monoalkanoyl-, 2'-monoalkanoyl- and 11,2'-dialkanoyl-4"-deoxy-4"-amino-oleandomycin reactants are prepared by reductive amination of the corresponding 11-monoalkanoyl-, 2'-monoalkanoyl- and 11,2'-dialkanoyl-4"-deoxy-4"-oxo-oleandomycins using palladium-on-charcoal, hydrogen (from about 1 to about 500 psi) and ammonium acetate in a suitable solvent such as methanol and isopropanol at about 20°-50° C. Alternatively, sodium cyanoborohydride can be used as reducing agent in place of palladium-on-charcoal and hydrogen. The de-esterified derivatives are conveniently prepared by solvolysis of the corresponding 2'-monoalkanoyl-4"-deoxy-4"-aminooleandomycins.

The necessary 4"-deoxy-4"-oxo-oleandomycin esters are prepared by selective oxidation of the 4"-hydroxy group using N-chlorosuccinimide and dimethylsulfide, followed by addition of a tertiary amine, such as triethylamine. The N-chlorosuccinimide and dimethylsulfide are combined in a reaction-inert solvent at about 0° C. After ten to twenty minutes, the temperature of the resulting mixture is adjusted to from about 0° C. to about −25° C., and the appropriate oleandomycin ester added. The reaction mixture is stirred for from about 2 to about 4 hours, after which the tertiary amine is added and the cooling bath removed. In order to accelerate the reaction, it is advantageous to employ from 1-20 fold excess of the N-chlorosuccinimide and the dimethylsulfide reactants. The tertiary amine is used in equimolar quantity to the N-chlorosuccinimide used. Suitable reaction-inert solvents for the reaction are toluene, benzene, ethyl acetate, chloroform, methylene chloride and tetrahydrofuran. Alternatively, dimethylsulfoxide-acetic anhydride or dimethylsulfoxidetrifluoroacetic anhydride are used as oxidizing agents.

The desired 4"-deoxy-4"-amino-oleandomycin derivatives are isolated by taking advantage of their basic nature. An aqueous solution of the crude amino derivative is extracted over a range of gradually increasing pH such that neutral or non-basic materials are extracted at lower pH's and the product at a pH of about 10. The extracting solvents, ethyl acetate or diethyl ether, are back washed with brine and water, dried over sodium sulfate, and evaporated to provide the product.

The necessary 4"-deoxy-4"-amino-erythromycin A and B and 4"-deoxy-4"-amino-erythromycin A 11,12-carbonate and 6,9-hemiketal can also be prepared by the above described reactions. Alternatively, the 4"-deoxy-4"-amino-erythromycins A and B, the 4"-deoxy-4"-amino-erythromycin A 11,12-carbonate 6,9-hemiketal are prepared by oxidation of the corresponding 4''-hydroxy derivative with one mole each of dimethylsulfoxide and trifluoroacetic anhydride in a reaction-inert solvent at about −30° C. to about −65° C., followed by treating the reaction mixture with about one mole of triethylamine. Methylene chloride is a suitable reaction-inert solvent for this oxidation. Representative procedures for preparing the necessary starting materials are provided below.

The stereochemistry of the starting materials leading to the antibacterial agents of the present invention is that of the natural material. Oxidation of the 4''-hydroxy groups of oleandomycin, erythromycins A and B, erythromycin A 11,12-carbonate 6,9-hemiketal ester to a ketone and a subsequent conversion of said ketone to the 4''-amines presents opportunity for the stereochemistry of the 4''-substituent to change from that of the natural product. Accordingly, when the 4''-oxo reactants are converted to amines, it is possible that epimeric amines are produced. In actual practice, it is observed that both epimeric amines are present in the final product in varying ratios depending upon the choice of synthetic method. If the isolated product consists predominantly of one of the epimers, said epimer can be purified by such methods as repeated crystallization from a suitable solvent to a constant melting point. The other epimer, the one present in smaller amount in the originally-isolated material, is the predominant product in the mother liquor. It can be recovered therefrom by methods known to those skilled in the art, such as, for example, by evaporation of the mother liquor and repeated recrystallization of the residue to a product of constant melting point or by chromatography. Although the mixture of epimeric amines can be separated by methods known to those skilled in the art, for practical reasons it is frequently advantageous to use said mixture as it is isolated from the reaction. Use of the epimeric mixture of 4''-amino reactants produces, of course, an epimeric mixture of the acylated products. The epimeric mixture thus produced can be separated by methods known to those skilled in the art. However, both epimers of a given compound exhibit the same type of activity and their separation, while desirable, is not always necessary.

In addition to the compounds described herein, compounds of formulae I–IV wherein Z is $(CH_2)_m$-(substituted heterocyclyl) wherein m is 0 or 1, heterocyclyl is as defined above and the substituent therein is chloro, bromo, alkyl having from one to four carbon atoms, alkoxy having from one to four carbon atoms; and those wherein Z is

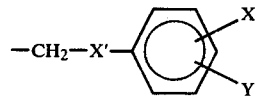

wherein X' is O or S; X and Y are as defined above, are also active as antibacterial agents in the same manner as are the compounds of formulae I–IV. Such compounds are conveniently prepared by the acylation procedures described herein.

Compounds of formulae I–IV herein exhibit in vitro activity against a variety of Gram-positive microorganisms and against certain Gram-negative microorganisms such as those of spherical or ellipsoidal shape (cocci). Their activity is readily demonstrated by in vitro tests against various microorganisms in a brain-heart infusion medium by the usual two-fold serial dilution technique. Their in vitro activity renders them useful for topical application in the form of ointments, creams and the like, for sterilization purposes, e.g. sick-room utensils; and as industrial antimicrobials, for example, in water treatment, slime control, paint and wood preservation.

For in vitro use, e.g. for topical application, it will often be convenient to compound the selected product with a pharmaceutically-acceptable carrier such as vegetable or mineral oil or an emollient cream. Similarly, they may be dissolved or dispersed in liquid carriers or solvents, such as water, alcohol, glycols or mixtures thereof or other pharmaceutically-acceptable inert media; that is, media which have no harmful effect on the active ingredient. For such purposes, it will generally be acceptable to employ concentrations of active ingredients of from about 0.01 percent up to about 10 percent by weight based on total composition.

Additionally, many compounds of this invention are active versus Gram-positive and certain Gram-negative microorganisms in vivo via the oral and/or parenteral routes of administration in animals, including man. Their in vivo activity is more limited as regards susceptible organisms and is determined by the usual procedure which comprises infecting mice of substantially uniform weight with the test organism and subsequently treating them orally or subcutaneously with the test compound. In practice, the mice, e.g. 10, are given an intraperitoneal inoculation of suitably diluted cultures containing approximately 1 to 10 times the $LD_{100}$ (the lowest concentration of organisms required to produce 100% deaths). Control tests are simultaneously run in which mice receive inoculum of lower dilutions as a check on possible variation in virulence of the test organism. The test compound is administered 0.5 hour post-inoculation, and is repeated 4, 24 and 48 hours later. Surviving mice are held for 4 days after the last treatment and the number of survivors is noted.

When used in vivo, these novel compounds can be administered orally or parenterally, e.g., by subcutaneous or intramuscular injection, at a dosage of from about 1 mg./kg. to about 200 mg./kg. of body weight per day. The favored dosage range is from about 5 mg./kg. to about 100 mg./kg. of body weight per day and the preferred range from about 5 mg./kg. to about 50 mg./kg. of body weight per day. Vehicles suitable for parenteral injection may be either aqueous such as water, isotonic saline, isotonic dextrose, Ringer's solution, or non-aqueous such as fatty oils of vegetable origin (cotton seed, peanut oil, corn, sesame), dimethylsulfoxide and other non-aqueous vehicles which will not interfere with therapeutic efficiency of the preparation and are nontoxic in the volume or proportion used (glycerol, propylene glycol, sorbitol). Additionally, compositions suitable for extemporaneous preparation of solutions prior to administration may advantageously be made. Such compositions may include liquid diluents; for example, propylene glycol, diethyl carbonate, glycerol, sorbitol, etc.; buffering agents, hyaluronidase, local anesthetics and inorganic salts to afford desirable pharmacological properties. These compounds may also be combined with various pharmaceutically-acceptable inert carriers including solid diluents, aqueous vehicles, non-toxic organic solvents in the form of capsules, tablets, lozenges, troches, dry mixes, suspensions, solutions, elixirs and parenteral solutions or suspensions. In general, the compounds are used in various dosage forms at concentration levels ranging from about 0.5 percent to about 90 percent by weight of the total composition.

In the Examples presented herein, no effort was made to recover the maximum amount of product produced or to optimize the yield of a given product. The Examples are merely illustrative of the process and of the products obtainable thereby.

In each of Examples 1–36, the 11-acetyl-4"-deoxy-4"-amino-oleandomycin reactant used is the major epimer produced according to Preparation E. The 11-acetyl-4"-deoxy-4"-amino-oleandomycin reactant of Examples 37 and 62 is the epimeric mixture of 4"-amino derivatives.

Examples 38–54 employ the single epimeric product of Preparation J as reactant. Since the configuration of the 4"-amino group is not known with certainty, the wavy line designation is used in the above formula.

Examples 55 and 63 use the epimeric 4"-deoxy-4"-amino-erythromycin A mixture of Preparation I as reactant.

EXAMPLE 1

11-Acetyl-4"-deoxy-4"-(2-phenylacetamido)oleandomycin

To a solution of 11-acetyl-4"-deoxy-4"-aminooleandomycin (2.88 g., 3.95 mmoles) in tetrahydrofuran (60 ml.) and water (30 ml.) at room temperature, adjusted to pH 8.0 by addition of dilute hydrochloric acid, is added a solution of phenylacetyl chloride (0.549 ml.) in tetrahydrofuran (4 ml.) dropwise with stirring over a period of three minutes. The pH is maintained at 7.9–8.1 by simultaneous addition of dilute aqueous sodium hydroxide (1 N). The reaction mixture is stirred for five minutes at room temperature and is then poured with stirring into a mixture of water-ethyl acetate (1:1), and the pH adjusted to 9.0. The organic phase is separated, washed with water, then with brine, and dried ($Na_2SO_4$). Evaporation of the solvent affords the product as a white foam (3.2 g.). The foam is dissolved in a hot solution of water (30 ml.)—acetone (45 ml.) and the resulting solution concentrated by boiling to approximately 60 ml. volume at which point the product begins to crystallize. The mixture is cooled, the solid filtered and vacuum dried. Yield=2.61 g., m.p. 154°–157° C.

NMR: $\delta_{CDCl_3}^{TMS}$ 7.36 (s, 5H), 5.80 (d, 1H), 3.66 (s, 2H), 3.40 (s, 3H), 2.66 (m, 2H), 2.35 (s, 6H), 2.06 (s, 3H).

EXAMPLES 2–24

Repetition of the procedure of Example 1, but using the appropriate acid chloride in place of phenacetyl chloride, affords the following compounds:

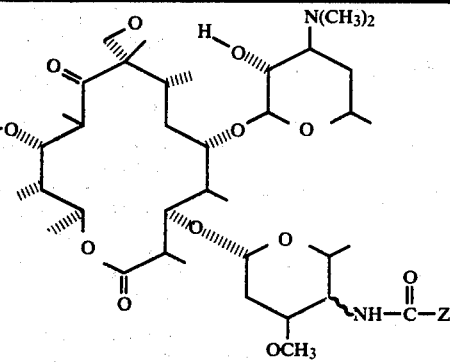

| Example | Z | M.P. (° C.) | NMR $\delta_{CDCl_3}^{TMS}$ |
|---|---|---|---|
| 2 | $CH_2-(3-ClC_6H_4)$ | 160–163.5 | 7.43 (m, 4H), 5.96 (d, 1H), 3.66 (s, 2H), 3.43 (s, 3H), 2.70 (m, 2H), 2.36 (s, 6H), 2.10 (s, 3H). |
| 3 | $CH_2-(4-ClC_6H_4)$ | 137–140 | 7.36 (s, 4H), 5.90 (d, 1H), 3.63 (s, 2H), 3.40 (s, 3H), 2.68 (m, 2H), 2.35 (s, 6H), 2.06 (s, 3H). |
| 4 | $CH_2-(2-FC_6H_4)$ | 161–164 | 7.33 (m, 4H), 5.91 (d, 1H), 3.70 (s, 2H), 3.40 (s, 3H), 2.68 (m, 2H), 2.35 (s, 6H), 2.08 (s, 3H). |
| 5 | $CH_2-(3-FC_6H_4)$ | 167.5–170 | 7.13 (m, 4H), 5.91 (d, 1H), 3.66 (s, 2H), 3.40 (s, 3H), 2.66 (m, 2H), 2.36 (s, 6H), 2.10 (s, 2H). |
| 6 | $CH_2-(4-FC_6H_4)$ | 159–162 | 7.16 (m, 4H), 5.90 (d, 1H), 3.66 (s, 2H), 3.41 (s, 3H), 2.68 (m, 2H), 2.36 (s, 6H), 2.08 (s, 3H). |
| 7 | $CH_2-(2-CH_3C_6H_4)$ | 182.5–186 | 7.28 (s, 4H), 5.63 (d, 1H), 3.66 (s, 2H), 3.40 (s, 3H), 2.68 (m, 2H), 2.35 (s, 9H), 2.06 (s, 3H). |
| 8 | $CH_2-(4-HOC_6H_4)$ | (white foam) | 7.03 (q, 4H), 6.00 (d, 1H), 3.63 (s, 2H), 3.43 (s, 3H), 2.70 (m, 2H), 2.38 (s, 6H), 2.10 (s, 3H). |
| 9 | $CH_2-(2-CH_3OC_6H_4)$ | 122–126 | 7.05 (m, 4H), 5.88 (d, 1H), 3.88 (s, 3H), 3.56 (bs, 2H), 3.31 (s, 3H), 2.61 (m, 2H), 2.31 (s, 6H), 2.05 (s, 3H). |
| 10 | $CH_2-(3-CH_3OC_6H_4)$ | 136.5–139.5 | 7.13 (m, 4H), 5.91 (d, 1H), 3.86 (s, 3H), 3.66 (s, 2H), 3.41 (s, 3H), 2.68 (m, 2H), 2.36 (s, 6H), 2.11 (s, 3H). |
| 11 | $CH_2-(4-CH_3OC_6H_4)$ | 109–112 | 7.10 (q, 4H), 5.88 (d, 1H), 3.85 (s, 3H), 3.61 (s, 2H), 3.41 (s, 3H), 2.65 (m, 2H), 2.35 (s, 6H), 2.08 (s, 3H). |
| 12 | $CH(Cl)-C_6H_5$ | (1:1 R,S | 7.43 (bs, 5H), 5.33 (s, 1H), 4.40 (s, 1.5H), |

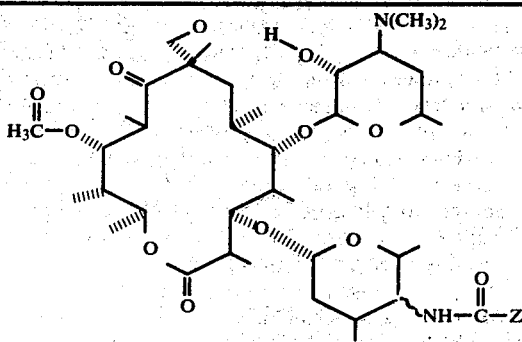

| Example | Z | M.P. (° C.) | NMR $\delta_{CDCl_3}^{TMS}$ |
|---|---|---|---|
| | | mixture; white foam | 3.33 (s, 1.5H), 2.66 (m, 2H), 2.30 (s, 6H), 2.06 (s, 3H). |
| 13 | 2-thenyl | 128–131 | 7.13 (m, 3H), 5.85 (d, 1H), 3.83 (s, 2H), 3.38 (s, 3H), 2.61 (m, 2H), 2.35 (s, 6H), 2.05 (s, 3H). |
| 14 | 3-thenyl | (a) | 7.16 (m, 3H), 5.90 (d, 1H), 3.63 (s, 2H), 3.36 (s, 3H), 2.63 (m, 2H), 2.33 (s, 6H), 2.06 (s, 3H). |
| 15 | 2-pyridylmethyl | 123.5–127.5 | 8.65 (d, 1H), 7.51 (m, 4H), 3.86 (s, 2H), 3.40 (s, 3H), 2.70 (m, 2H), 3.36 (m, 6H), 2.10 (s, 3H). |
| 16 | 3-pyridylmethyl | 157–160 | 8.60 (m, 2H), 7.73 (m, 2H), 6.28 (d, 1H), 3.66 (s, 2H), 3.41 (s, 3H), 2.68 (m, 2H), 2.36 (s, 6H), 2.06 (s, 3H). |
| 17 | 1-tetrazolylmethyl | 142–146(b) | 8.96 (s, 1H), 3.33 (s, 3H), 2.70 (m, 2H), 2.30 (s, 6H), 2.03 (s, 3H). |
| 18 | $CH_2-(2-CF_3C_6H_4)$ | 170–172 (dec.) | 7.63 (m, 4H), 5.81 (d, 1H), 3.88 (s, 2H), 3.40 (s, 3H), 2.68 (m, 2H), 2.35 (s, 6H), 2.08 (s, 3H). |
| 19 | $D(-)CH(OH)C_6H_5$ | 135–138 | 7.43 (m, 5H), 6.91 (d, 1H), 5.16 (s, 1H), 3.40 (s, 3H), 2.65 (m, 2H), 2.35 (s, 6H), 2.06 (s, 3H). |
| 20 | D,L $CH(OCH_3)C_6H_5$ | (white foam) | 7.40 (m, 5H), 7.03 (d, 1H), 3.46 (s, 1.5H), 3.43 (s, 1.5H), 3.40 (s, 1.5H), 3.23 (s, 1.5H), 2.68 (m, 2H), 2.36 (s, 6H), 2.10 (2, 3H). |
| 21 | $CH_2-(3-CF_3C_6H_4)$ | 115–119 | 7.60 (m, 4H), 5.96 (d, 1H), 3.76 (s, 2H), 3.43 (s, 3H), 2.70 (m, 2H), 2.36 (s, 6H), 2.10 (s, 3H). |
| 22 | $CH_2-(2-ClC_6H_4)$ | 175–178.5 | 7.31 (m, 4H), 5.73 (d, 1H), 3.76 (s, 2H), 3.35 (s, 3H), 2.61 (m, 2H), 2.33 (s, 6H), 2.03 (s, 3H). |
| 23 | $CH(NH_2)C_6H_5$ | 60–165 | 7.33 (m, 5H), 4.53 (s, 1H), 3.36 (s, 2.4H), 3.25 (s, 0.6H), 2.63 (m, 2H), 2.33 (s, 6H), 2.06 (s, 3H). |
| 24 | $CH_2-C(CH_3)_3$ | foam | 5.61 (d, 1H), 3.43 (s, 3H), 2.68 (m, 2H), 2.36 (s, 6H), 2.16 (s, 2H), 2.10 (s, 3H). |

(a) CHCl₃ solution of reaction product subjected to column chromatography on silica gel (40 g./1.1 g. of crude product) using CHCl₃ as eluant.
(b) product extracted at pH 10.1.

EXAMPLE 25

L(+)-11-Acetyl-4"-deoxy-4"-(1-hydroxy-2-phenylacetamido)oleandomycin

N-hydroxysuccinimide (296 mg., 2.97 mmoles) is added with stirring to a solution of L(+)-mandelic acid (391 mg., 2.57 mmoles) in tetrahydrofuran (20 ml.). When solution is complete, dicyclohexylcarbodiimide (531 mg., 2.57 mmoles) is added. The reaction mixture is stirred for one hour at room temperature and is then filtered to remove dicyclohexylurea. The filter cake is washed with tetrahydrofuran (5 ml.) and the combined filtrate and wash solution treated with 11-acetyl-4"-deoxy-4"-amino-oleandomycin (1.5 g., 2.05 mmoles) under an atmosphere of nitrogen at room temperature. The reaction mixture is stirred for one hour and is then poured into a mixture of methylene chloride—water (1:1). The organic phase is separated, combined with an equal volume of water and, with stirring, the pH adjusted to 10.5. The organic phase is separated and washed successively with water and brine and is then dried (Na₂SO₄). Evaporation of the extract affords the crude product as a white foam (1.51 g.). The foam is dissolved in a hot solution of acetone (20 ml.)—water (20 ml.) and the resulting solution evaporated at atmospheric pressure by boiling until it becomes turbid. The concentrate is stirred for 1.5 hours at room temperature after which the solid is removed by filtration and dried at 60° C. in high vacuum. Yield=962 mg. of white crystals. M.P. 236.5°–240° C. (dec.).

NMR: $\delta_{CDCl_3}^{TMS}$ 7.45 (m, 5H), 6.91 (d, 1H), 5.16 (s, 1H), 3.31 (s, 3H), 2.68 (m, 2H), 2.35 (s, 6H), 2.08 (s, 3H).

EXAMPLE 26

11-Acetyl-4''-deoxy-4''-(pivaloylamido)oleandomycin

To a solution, at room temperature, of 1H-tetrazolyl-1-acetic acid (795 mg., 5.92 mmoles) in tetrahydrofuran (10 ml.) is added with stirring pivaloyl chloride (0.728 ml., 5.92 mmoles). The mixture becomes turbid and is stirred for 15 minutes. It is then added dropwise (5.5 ml.) with stirring to a solution of 11-acetyl-4''-deoxy-4''-amino-oleandomycin (1.5 g., 2.05 mmoles) in water (15 ml.) and tetrahydrofuran (30 ml.) at room temperature and pH 8.0. The pH is maintained at 7.9–8.1 by simultaneous addition of 1 N NaOH as needed. The reaction mixture is then poured into a stirring mixture of ethyl acetate—water and the pH adjusted to 10.5. The organic phase is separated, washed successively with water and brine and then dried ($Na_2SO_4$). Evaporation of the solvent gives the product as a white foam (1.52 g.).

NMR: $\delta_{CDCl_3}^{TMS}$ 5.83 (d, 1H), 3.38 (s, 3H), 2.66 (m, 2H), 2.33 (s, 6H), 2.08 (s, 3H), 1.10 (s, 9H).

EXAMPLES 27–36

11-Acetyl-4''-deoxy-4''-(2-fluorobenzamido)oleandomycin

To a solution of 11-acetyl-4''-deoxy-4''-aminooleandomycin (1.50 g., 2.05 mmoles) in tetrahydrofuran (35 ml.) and water (15 ml.) at room temperature, adjusted to pH 8.0 by addition of dilute hydrochloric acid, is added a solution of 2-fluorobenzoyl chloride (0.27 ml.) in tetrahydrofuran (5 ml.) dropwise with stirring over a period of three minutes. The pH is maintained at 7.9–8.1 by simultaneous addition of dilute aqueous sodium hydroxide (1 N). The reaction mixture is stirred for five minutes at room temperature and is then poured with stirring into a mixture of water—ethyl acetate (1:1), and the pH adjusted to 9.0. The organic phase is separated, washed with water, then with brine, and dried ($Na_2SO_4$). Evaporation of the solvent affords the product as a white foam (1.61 g.).

NMR: $\delta_{CDCl_3}^{TMS}$ 7.40 (m, 4H), 3.50 (s, 3H), 2.70 (m, 2H), 2.38 (s, 6H), 2.10 (s, 3H).

The following compounds are prepared in like manner from appropriate acid chlorides [Z-C(O)Cl] and 11-acetyl-4''-deoxy-4''-amino-oleandomycin.

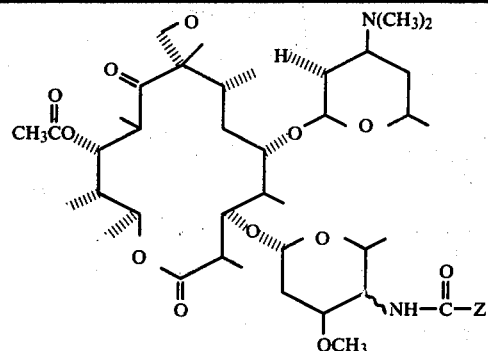

| Example | Z | NMR $\delta_{CDCl_3}^{TMS}$ |
|---|---|---|
| 28 | $C_6H_5$ | 7.48 (m, 4H), 6.33 (d, 1H), 3.43 (s, 3H), 2.66 (m, 2H), 2.33 (s, 6H), 2.06 (s, 3H). |
| 29 | 2-$CH_3OC_6H_4$ | 7.26 (m, 4H), 4.03 (s, 3H), 3.50 (s, 3H), 2.70 (m, 2H), 2.36 (s, 6H), 2.10 (s, 3H). |
| 30 | 2-$CH_3OC(O)C_6H_4$ | 7.56 (m, 4H), 6.13 (d, 1H), 3.91 (s, 3H), 3.51 (s, 3H), 2.68 (m, 2H), 2.38 (s, 6H), 2.06 (s, 3H). |
| 31 | 2-$ClC_6H_4$ | 7.38 (m, 4H), 6.35 (d, 1H), 3.45 (s, 3H), 2.63 (m, 2H), 2.33 (s, 6H), 2.05 (s, 3H). |
| 32 | 2-$CF_3C_6H_4$ | 7.53 (m, 4H), 6.05 (d, 1H), 3.43 (s, 3H), 2.63 (m, 2H), 2.31 (s, 6H), 2.03 (s, 3H). |
| 33 | 2-furyl | 7.46 (m, 1H), 7.10 (m, 1H), 6.50 (m, 2H), 3.43 (s, 3H), 2.65 (m, 2H), 2.33 (s, 6H), 2.06 (s, 3H). |
| 34 | 2-thienyl | 7.55 (m, 2H), 7.08 (m, 1H), 6.26 (d, 1H), 3.45 (s, 3H), 2.68 (m, 2H), 2.35 (s, 6H), 2.08 (s, 3H). |
| 35 | 2-(1-methylpyrrolyl) | 6.70 (m, 2H), 6.06 (m, 2H), 3.96 (s, 3H), 3.45 (s, 3H), 2.68 (m, 2H), 2.40 (s, 6H), 2.10 (s, 3H). |
| 36 | 3-thienyl | 7.93 (m, 1H), 7.38 (m, 2H), 6.15 (d, 1H), 3.45 (s, 3H), 2.68 (m, 2H), 2.38 (s, 6H), 2.08 (s, 3H). |

EXAMPLE 37

The following compounds are prepared from appropriate acid chlorides [Z-C(O)-Cl] and oleandomycins according to the procedure of Example 27.

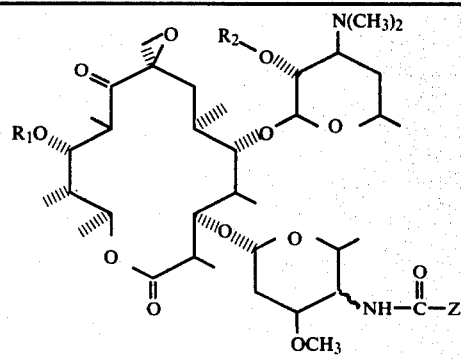

| $R_1$ | $R_2$ | Z |
|---|---|---|
| Ac | H | 2-$BrC_6H_4$ |
| Ac | H | 4-$ClC_6H_4$ |
| Ac | H | 2,6-$Cl_2C_6H_3$ |
| Ac | H | 2,4-$Cl_2C_6H_3$ |
| Pr | H | 3-$BrC_6H_4$ |
| Pr | H | 2,4-$F_2C_6H_3$ |

-continued

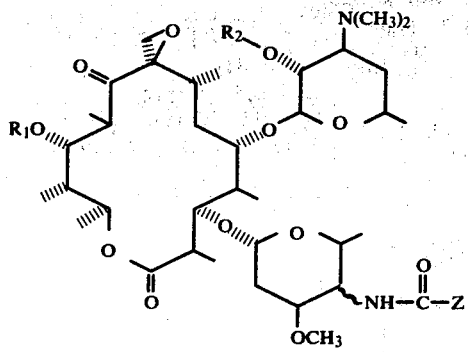

| R₁ | R₂ | Z |
|---|---|---|
| Ac | Ac | 4-Br-3-ClC₆H₃ |
| Pr | Pr | 3-Br-4-FC₆H₃ |
| Pr | Pr | 3-Cl-5-F-C₆H₃ |
| H | H | 4-(CF₃)C₆H₄ |
| Ac | Ac | 5-Cl-2-(C₂H₅O)C₆H₃ |
| Ac | H | 2-(n-C₄H₉O)-5-ClC₆H₃ |
| H | Pr | 2,3-(CH₃O)₂C₆H₃ |
| H | Ac | 5-Br-2-(i-C₃H₇O)C₆H₃ |
| H | H | 2,6-(CH₃O)₂C₆H₃ |
| Pr | Pr | 3-(n-C₄H₉)-4-HOC₆H₃ |
| Ac | Ac | 3-Cl-4-HOC₆H₃ |
| Ac | H | 3-Cl-4-CH₃C₆H₃ |
| H | H | 2-F-4-CH₃C₆H₃ |
| Ac | H | 6-Cl-2-(CF₃)C₆H₃ |
| Pr | H | 2-(t-C₄H₉)-4-(i-C₃H₇)C₆H₃ |
| Pr | H | 6-C₂H₅O-3-CH₃C₆H₃ |
| Ac | H | 2-(n-C₄H₉O)C₆H₄ |
| Ac | H | 2,6-F₂C₆H₃ |
| Ac | H | 4-CH₃OCOC₆H₄ |
| Ac | H | 4-(n-C₄H₉OCO)C₆H₄ |
| H | H | 3-C₂H₅OCOC₆H₄ |
| Ac | H | 2-CH₃OCO-4-BrC₆H₃ |
| Pr | Pr | 2-C₂H₅OCO-4-n-C₄H₉OC₆H₃ |
| Pr | H | 2-CH₃OCO-3-CH₃OC₆H₃ |
| Ac | Ac | 2-C₂H₅OCO-3-ClC₆H₃ |
| Ac | H | 2-CH₃OCO-4-CH₃C₆H₃ |
| Ac | H | 4-CH₃OCO-2-ClC₆H₃ |
| Pr | Pr | 4-C₂H₅OCO-2-CH₃C₆H₃ |
| Ac | H | 3-furyl |
| Ac | H | 2-pyridyl |
| Ac | H | 3-pyridyl |
| Ac | H | 4-pyridyl |
| Ac | H | 4-oxazolyl |
| Ac | Ac | 5-oxazolyl |
| Pr | H | 2-oxazolyl |
| Ac | H | 5-oxazolyl |
| Pr | H | 4-thiazolyl |
| H | H | 5-thiazolyl |
| Ac | H | 4-thiazolyl |
| H | Ac | 2-(N-methylpyrrolyl) |
| Ac | H | 4-(N-methylpyrrolyl) |
| Pr | H | 2-imidazolyl |
| Ac | Ac | 4-imidazolyl |
| Pr | Pr | 5-imidazolyl |
| Ac | H | 2-pyrrolyl |
| Ac | H | 2-furfuryl |
| H | H | 2-thenyl |
| H | H | 3-thenyl |
| Pr | H | CH₂-(4-oxazolyl) |
| H | Ac | CH₂-(5-oxazolyl) |
| H | Pr | CH₂-(5-thiazolyl) |

-continued

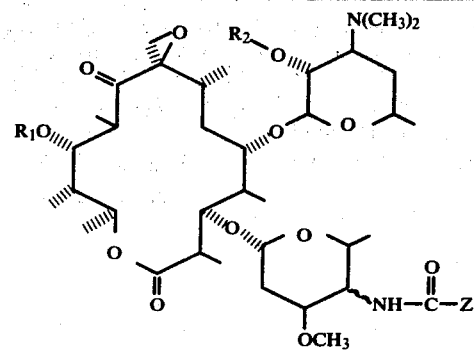

| R₁ | R₂ | Z |
|---|---|---|
| Ac | H | CH₂-(2-pyrrolyl) |
| Ac | H | CH₂-(2-pyridyl) |
| Ac | H | CH₂-(4-pyridyl) |
| Ac | Ac | CH₂-[2-(N-CH₃-pyrrolyl)] |
| Ac | H | CH₂C(CH₃)₃ |
| H | H | CH₂C(CH₃)₃ |
| Ac | H | 2-pyrazinyl |
| Ac | H | 3-isoxazolyl |
| Pr | Pr | 5-isoxazolyl |
| Pr | H | 3-isoxazolyl |
| Ac | H | 5-methyl-3-isoxazolyl |
| Ac | H | 3-methyl-5-isoxazolyl |
| Ac | H | 5-isothiazolyl |
| Pr | Pr | 4-isothiazolyl |
| Pr | H | 2-methyl-4-thiazolyl |
| Ac | Ac | 2-methyl-5-thiazolyl |
| Ac | Ac | 4-(1,2,3-thiadiazolyl) |
| Ac | Ac | 2-methyl-4-oxazolyl |
| Ac | Ac | 2-pyrazinyl |
| Ac | H | CH₂-(4-methyl-2-thiazolyl) |
| Pr | H | CH₂-(2-methyl-4-thiazoyl) |
| Pr | Pr | CH₂-(3-methyl-5-isoxazolyl) |
| Ac | Ac | CH₂-(3-pyridyl) |
| Ac | Pr | CH₂-(3-methyl-5-isothiazolyl) |
| Pr | Ac | CH₂-(5-isoxazolyl) |
| Ac | H | CH₂-(2-pyrrolyl) |
| Ac | Ac | CH₂-(4-imidazolyl) |
| Ac | H | CH₂-(4-imidazolyl) |
| Ac | H | 6-methyl-2-pyrazinyl |
| Ac | H | 5-methyl-2-furyl |
| Ac | H | 5-methyl-3-furyl |
| Pr | H | 3-methyl-2-furyl |
| Pr | Pr | 4-methyl-2-thienyl |
| Ac | Ac | 5-methyl-3-thienyl |
| Ac | Ac | CH₂-(1-pyrrolyl) |
| Ac | H | 2-methyl-4-imidazolyl |
| Ac | H | CH₂-(1-imidazolyl) |
| Br | H | N-methyl-2-pyrrolyl |
| Ac | H | 2-methyl-3-pyridyl |
| Ac | H | 2-methyl-4-pyridyl |
| Ac | H | 6-methyl-2-pyridyl |
| Ac | Ac | 4-methyl-2-pyridyl |
| Pr | H | 5-methyl-2-pyridyl |

EXAMPLES 38–56

The procedure of Example 1 is repeated but using 4″-deoxy-4″-amino-erythromycin A as the macrolide reactant and the appropriate acid chlorides to give the following compounds:

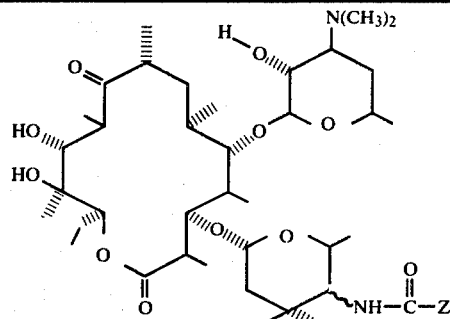

| Example | Z | M.P. (°C.) | NMR $\delta_{CDCl_3}^{TMS}$ |
|---|---|---|---|
| 38 | $CH_2-C_6H_5$ | 138–144 (single) epimer) | 7.45 (s, 5H), 5.83 (d, 1H), 3.68 (s, 2H), 3.35 (s, 3H), 2.38 (2, 6H), 1.46 (s, 3H). |
| 39 | $CH_2C_6H_5$ (epimer of Ex. 38) | (white foam) | 7.63 (s, 5H), 6.03 (d, 1H), 3.63 (s, 2H), 3.25 (s, 3H), 2.43 (s, 6H), 1.45 (s, 3H). |
| 40 | $CH_2-(3-ClC_6H_4)$ | (white foam) | 7.30 (m, 4H), 6.13 (d, 1H), 3.60 (s, 2H), 3.30 (s, 3H), 2.35 (s, 6H), 1.43 (s, 3H). |
| 41 | $CH_2-(2-CH_3OC_6H_4)$ | (white foam) | 7.16 (m, 4H), 6.36 (d, 1H), 3.93 (s, 3H), 3.66 (s, 2H), 3.33 (s, 3H), 2.36 (s, 6H), 1.46 (s, 3H). |
| 42 | $C(CH_3)_3$ | (white foam) | 5.90 (d, 1H), 3.33 (s, 3H), 2.35 (s, 6H), 1.46 (s, 3H). |
| 43 | $CH(Cl)-C_6H_5$ | 1:1 R,S mixture (white foam) | 7.63 (m, 5H), 6.91 (d, 1H), 5.53 (s, 1H),Z 3.36 (s, 3H), 2.38 (s, 6H), 1.50 (s, 3H). |
| 44 | $CH_2-(3-FC_6H_4)$ | (white foam) | 7.10 (m, 4H), 6.00 (d, 1H), 3.60 (s, 2H), 3.30 (s, 3H), 2.30 (s, 6H), 1.45 (s, 3H). |
| 45 | 3-thenyl | (pale yellow foam) | 7.16 (m, 3H), 5.95 (d, 1H), 3.63 (s, 2H), 3.26 ) (s, 3H), 2.31 (s, 6H), 1.43 (s, 3H). |
| 46 | 2-thenyl | (pale yel- | 7.38 (m, 1H), 7.06 (m, 2H), 6.01 (d, 1H), 3.88 (s, 2H), 3.33 (s, 3H), 2.40 (s, 6H), 1.43 (s, 3H). |
| 47 | $CH_2-(2-FC_6H_4)$ | 161–164 | 7.10 (m, 4H), 5.90 (d, 1H), 3.63 (s, 2H), 3,28 (s, 3H), 2.33 (s, 6H), 1.45 (s, 3H). |
| 48 | $CH_2-(3-CH_3OC_6H_4)$ | (ivory foam) | 7.38 (m, 1H), 6.90 (m, 3H), 5.90 (d, 1H), 3.85 (s, 3H), 3.63 (s, 2H), 3.33 (s, 3H), 2.36 (s, 6H), 1.46 (s, 3H). |
| 49 | $D,L-CH(OCH_3)C_6H_5$ | (white foam) | 7.46 (m, 5H), 6.98 (d, 1H), 6.40 (s, 1H), 3.46 (s, 1.5H), 3.43 (s, 1.5H), 3.36 (s, 1.5H), 3.31 (s, 1.5H), 2.38 (s, 6H). |
| 50 | $CH_2-(3-CF_3C_6H_4)$ | | 7.63 (bs, 3H), 7.40 (s, 1H), 6.08 (d, 1H), 3.71 (s, 2H), 3.33 (s, 6H), 1.45 (s, 3H). |
| 51 | $CH_2-(2-ClC_6H_4$ | | 7.30 (m, 4H), 5.80 (d, 1H), 3.75 (s, 2H), 3.26 (s, 3H), 2.36 (s, 6H), 1.43 (s, 3H). |
| 52 | $CH_2-(2-CH_3C_6H_4)$ | | 7.35 (m, 4H), 5.85 (d, 1H), 3.61 (s, 2H), 3.31 (s, 3H), 2.36 (s, 6H), 1.45 (s, 3H). |
| 53 | 2-furyl | 147–151 | 7.56 (bs, 1H), 7.20 (bs, 1H), 6.63 (m, 2H), 3.40 (s, 3H), 2.40 (s, 6H), 1.50 (s,3H). |
| 54 | 2-thienyl | | 7.60 (m, 2H), 7.11 (m, 1H), 6.31 (d, 1H), 3.38 (s, 3H), 2.38 (s, 6H), 1.48 (s, 3H). |
| 55 | $CH_2-(3,4-Cl_2C_6H_3)$ | 145.5–149 | 7.36 (m, 3H), 6.40 (d, 1H), 3.60 (s, 2H), 3.33 (s, 3H), 2.30 (s, 6H), 1.46 (s, 3H). |
| 56 | 2-methyl-4-thiazolyl | | 7.91 (s, 1H), 7.53 (d, 2H), 3.35 (s, 3H), 2.71 (s, 3H), 2.31 (s, 6H), 1.48 (s, 3H). |

EXAMPLE 57

The procedure of Example 38 is followed but using the appropriate acid halide to provide the compounds listed below:

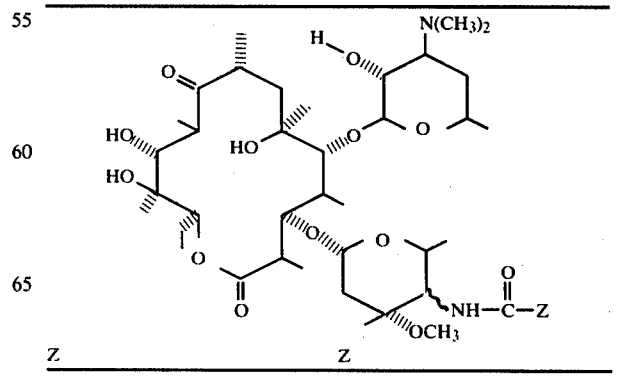

CH2-(4-n-C4H9OC6H4)
CH2-(3-C2H5OC6H4)
CH2-(3-BrC6H4)
CH2-(4-t-C4H9C6H4)
CH2-(2-CH3C6H4)
CH2(2-CH3OC6H4)
CH(OH)C6H5
CH(NH2)C6H5
CH(NH2)-4-ClC6H4
CH(NH2)-2-BrC6H4
CH(NH2)-4-CH3OC6H4
CH(NH2)-4-t-C4H9C6H4
CH(NH2)-4-FC6H4
CH(OCH3)-3-CH3C6H4
CH(OCH3)-2-ClC6H4
CH2-2-(2,4-F2C6H3)
CH2-(2,6-Cl2C6H3)
CH2-(4-Cl-3-CF3C6H3)
CH2-(4-n-C4H9O-3-CH3C6H3)
CH(Cl)-3,5-(C2H5O)2C6H3
CH2-3,4-(HO)2C6H3
CH(Cl)-5-Cl-2-HOC6H3
CH(OCH3)-6-Cl-3-CF3C6H3
C6H5
2-ClC6H4
2-CH3OC6H4
4-n-C4H9OC6H4
3-BrC6H4
3-C2H5C6H4
4-t-C4H9C6H4
CH(CH3)C6H5
CH(CH3)-2-ClC6H4
CH(n-C4H9)C6H5
CH(CH3)-4-CH3OC6H4
CH(C2H5)-2-CH3OCOC6H4
CH(CH3)-3-CF3C6H4
CH(n-C3H7)-2,6-Cl2C6H3
CH(CH3)-2-CH3OC6H4
CH(n-C4H9)-3-i-C3H7C6H4
CH(CH3)-4-FC6H4
2-furfuryl
CH2-(2-imidazolyl)
CH2-(2-oxazolyl)
3-pyridyl
4-pyridyl
CH2-(3-pyridyl)
2-pyrazinyl
3-isoxazolyl
CH2-(4-pyridyl)
CH2(5-oxazolyl)
4-(N-methylpyrrolyl)
CH2(1-pyrrolyl)
3-methyl-2-furyl
3-methyl-2-thienyl
1-methyl-4-imidazolyl
5-methyl-4-imidazolyl
4-methyl-2-pyridyl
2-methyl-4-pyridyl CH(O-n-C4H9)C6H5
CH(OC2H5)C6H5
CH(O-n-C4H9)-2-ClC6H4
CH(O-n-C3H7)-4-FC6H4
CH(OCH3)-3-C2H5C6H4
CH(OH)-2-ClC6H4
CH(OH)-4-BrC6H4
CH(OH)-4-CH3C6H4
CH(OH)-4-n-C4H9OC6H4
CH(Cl)-2-ClC6H4
CH(Cl)-3-C2H5C6H4
CH(Cl)-4-CF3C6H5
CH(Cl)-2-CH3OCOC6H4
CH(OCH3)-4-CF3C6H4
CH(OH)-2,6-Cl2C6H3
4-FC6H4
2,4-F2C6H3
2,6-Cl2C6H3
5-Br-2-i-C4H9OC6H3
3-CH3O-4-n-C4H9OC6H3
5-Cl-2-C2H5OC6H3
2-HOC6H4
2,3-(HO)2C6H3
4-Cl-2-HOC6H3
6-Cl-3-CF3C6H3
2-CH3OCOC6H4
2-CH3OCO-4-CH3C6H3
2-C2H5OCO-3-ClC6H3
2-CH3OCO-3-CH3OC6H3
2-CH3OCO-4-n-C4H9OC6H3
CH2-(4-oxazolyl)
CH2-(5-thiazolyl)
CH2-(2-pyrrolyl)
CH2-(4-pyridyl)
CH2-[2-(N-CH3-pyrrolyl)]
4-oxazolyl
5-oxazolyl
3-pyridyl
5-thiazolyl
2-thiazolyl
3-furyl
3-thienyl
CH2C(CH3)3
4-methyl-5-oxazolyl
4-methyl-5-thiazolyl
4-(1-thia-2,3-diazolyl)
4-imidazolyl
CH2-(5-isoxazolyl)
CH2-(4-imidazolyl)
CH2(3-methyl-5-isothiazolyl)
CH2(3-methyl-5-isoxazolyl)
CH2(4-methyl-2-thiazolyl)
6-methyl-2-pyrazinyl
4-methyl-2-pyrrolyl
5-methyl-2-pyrrolyl
CH2(1-imidazolyl)
2-methyl-3-pyridyl

EXAMPLE 58

4″-Deoxy-4″-(2-phenylacetamido)erythromycin A 11,12-Carbonate Ester 6,9-Hemiketal Phenacetyl chloride (1.52 mmoles) and 4″-deoxy-4″-amino-erythromycin A 6,9-hemiketal 11,12-carbonate ester (1.45 mmoles) are reacted according to the procedure of Example 1. The reaction mixture is poured into water—ethyl acetate and the pH of the resulting mixture adjusted to 5. The ethyl acetate layer is separated and added to an equal volume of water. The pH is adjusted to 9.5 with stirring, the ethyl acetate phase separated, washed first with water, then with brine and dried (Na2SO4). Removal of the solvent under reduced pressure gives the product as a mixture of epimer A and epimer B forms (953 mg.). The product is chromatographed on a silica gel (40 g.) column, loaded with and eluted with chloroform—acetone (3:1) and fractions of 800 drops each collected. Fractions 6–60 are combined and evaporated to dryness to give one epimer (A) of the title product as an ivory foam (370 mg.). Fractions 101–150 are combined to give the other epimer (107 mg.) as an ivory foam. Fractions 61–100 contain a mixture of epimers (114 mg.) and are not worked up further.

NMR: $\delta_{CDCl_3}^{TMS}$:

Epimer A: 7.38 (s, 5H), 5.88 (d, 1H), 3.63 (s, 2H), 3.21 (s, 3H), 2.35 (s, 6H), 1.61 (s, 3H).

Epimer B: 7.43 (s, 5H), 5.85 (d, 1H), 3.65 (s, 2H), 3.31 (s, 3H), 2.31 (s, 6H), 1.63 (s, 3H).

EXAMPLE 59

The procedure of Example 58 is repeated but using the appropriate acid chloride Z—C(O)—Cl in place of phenacetyl chloride to give the compounds tabulated below.

| Z | Z |
|---|---|
| 2-CH3C6H4 | 4-F-3-CH3C6H3 |
| 4-n-C4H9OC6H4 | 2,4-t-C4H9C6H3 |
| 2-ClC6H4 | 3-CF3C6H4 |
| 3-BrC6H4 | 4-CH3OCOC6H4 |
| 4-ClC6H4 | 2-CH3OCO-4-CH3C6H3 |
| 3-C2H5OC6H4 | 2-i-C3H7O-5-BrC6H5 |
| 3-CH3C6H4 | 6-Cl-2-CF3C6H3 |
| 4-t-C4H9C6H4 | 3,4-(C2H5O)2C6H3 |
| 4-FC6H4 | CH2-(4-ClC6H4) |
| 2,6-F2C6H3 | CH2-(3-CF3C6H4) |
| 2,6-Cl2-C6H3 | CH2-(2,6-Cl2C6H4) |
| 2-HOC6H3 | CH2-[2,4-(CH3)2C6H3] |
| 3-Br-5-HOC6H3 | CH2-[2,3-(HO)2C6H3] |
| 2,4-(HO)2C6H3 | CH2-(2-CH3OC6H4) |
| 3-Cl-4-HOC6H3 | CH2-(4-n-C5H9OCOC6H4) |
| CH(Cl)C6H5 | 2-furfuryl |
| CH(Cl)-2-ClC6H4 | 3-thienyl |
| CH(Cl)-2-CH3OC6H4 | 3-thenyl |
| CH(NH2)C6H5 | 2-furyl |
| CH(OCH3)C6H5 | 2-imidazolyl |
| 5-oxazolyl | 5-thiazolyl |
| CH(O-n-C4H9)C6H5 | 2-pyridyl |
| CH(CH3)C6H5 | 4-pyridyl |
| CH(CH3)-3-CF3C6H4 | 2-pyrrolyl |
| CH(CH3)-2-CH3OC6H4 | 4-oxazolyl |
| CH(OH)C6H5 | 2-thiazolyl |
| CH(OH)-4-ClC6H4 | 2-(N-CH3-pyrrolyl) |
| CH(OH)-2,6-Cl2C6H3 | CH2-(2-imidazolyl) |
| CH(OCH3)-4-FC6H4 | CH2-(4-oxazolyl) |
| CH2-(3-pyridyl) | CH2C(CH3)3 |
| CH2-(2-thiazolyl) | C(CH3)3 |
| CH2-(5-oxazolyl) | CH2-(4-methyl-2-thiazolyl) |
| CH2(5-isoxazolyl) | CH2-(4-methyl-5-oxazolyl) |
| 2-pyrazinyl | CH2-(4-methyl-5-thiazolyl) |
| 4-isothiazolyl | 4-(L-thia-2,3-diazolyl) |
| 3-furyl | 5-methyl-3-isoxazolyl |
| 3-isoxazolyl | 4-methyl-5-oxazolyl |
| 4-thiazolyl | 4-methyl-5-thiazolyl |
| 3-methyl-2-furyl | 6-methyl-2-pyrazinyl |
| 4-methyl-2-thienyl | 5-methyl-4-imidazolyl |
| 5-methyl-3-thienyl | N-methyl-2-pyrrolyl |
| CH2-(1-imidazolyl) | 5-methyl-2-pyrrolyl |
| CH2-(4-imidazolyl) | 1-methyl-4-imidazolyl |

-continued

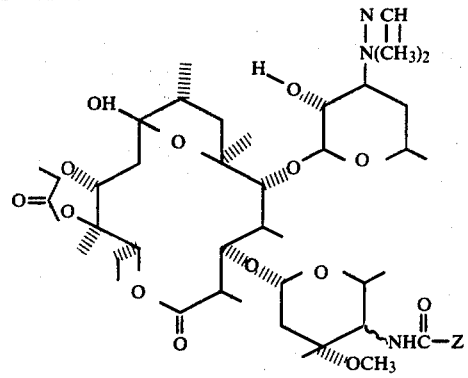

| Z | Z |
|---|---|
| 6-methyl-2-pyridyl | 3-methyl-5-isothiazolyl |
| 5-methyl-2-pyridyl | 2-methyl-4-pyridyl |

EXAMPLES 60–64

4"-Deoxy-4"-pivaloylamido-9(S)-erythromycylamine

A mixture of 4"-deoxy-4"-pivaloylamido-erythromycin A (1.5 g., 1.83 mmoles), anhydrous hydrazine (0.582 ml., 18.3 mmoles) and methanol (35 ml.) is refluxed overnight under a nitrogen atmosphere. A second portion of anhydrous hydrazine (0.582 ml.) is then added and the mixture refluxed an additional 6 hours. The mixture is evaporated to dryness under reduced pressure to give the hydrazone as a white foam (1.52 g.).

To the hydrazone (0.760 g., 0.915 mmoles) in methanol (20 ml.) is added a solution of sodium nitrite (316 mg.) in water (2 ml.). The mixture is stirred and cooled to 0°–5° C. and then treated dropwise with hydrochloric acid (2.04 ml. of 3 N, 6.15 mmoles) at such a rate that the temperature does not rise above 10° C. or the pH drop below 4.0. The mixture is stirred for 5 minutes following completion of the HCl addition and is then adjusted to pH 8 by addition of 4 N NaOH. Sodium borohydride (27.4 mg., 0.72 mmoles) is then added and the reaction mixture stirred at 5°–10° C. for 30 minutes. The pH is then lowered to 2.5 by addition of 6 N HCl and the mixture stirred for 10 minutes at 5°–10° C. Water (75 ml.) and methylene chloride (25 ml.) are added to the reaction mixture and the pH adjusted to 10.5. The methylene chloride phase is separated and the aqueous phase extracted with methylene chloride (×25 ml.). The combined extracts are washed with brine (1×25 ml.), dried (Na$_2$SO$_4$) and evaporated to dryness to give the crude product as a foam (683 mg.).

The crude product is dissolved in the minimal volume of methylene chloride—water 91:1) and extracted at pH values of 2.5, 3.3 and 10.0 (Thin layer chromatography in the system 6 CHCl$_3$—1 CH$_3$OH—0.1 NH$_4$OH shows the desired product is in the pH 10 extract). The pH 10 extract is dried (Na$_2$SO$_4$) and evaporated under reduced pressure to give a white foam (341 mg.). It is purified by dissolution in water (30 ml.)—ethyl acetate (30 ml.) and extraction of the mixture at pH 4.8. The organic phase is separated, fresh ethyl acetate added and the extraction process repeated at pH values of 5.5, 5.8 and 10.0. The pH 10 extract is dried (Na$_2$SO$_4$), evaporated to dryness and a chloroform solution of the residue chromatographed on a formamide impregnated silica gel (12 g.) column using chloroform as eluant. Five ml. fractions are collected. Fractions 4–30 are combined, evaporated to dryness and the residue dissolved in water (30 ml.)—ethyl acetate (30 ml.) The mixture is extracted as described above but at pH values of 6.0, 6.5, 6.8 and 10. The pH 10 extract is dried (Na$_2$SO$_4$) and evaporated at reduced pressure to give a tacky foam. The foam is dissolved in methylene chloride (30 ml.) and extracted with water (2×30 ml.) at pH 10. The methylene chloride solution is then dried and evaporated under reduced pressure to give the title product as a white foam (123 mg.).

NMR: $\delta_{CDCl_3}^{TMS}$ 5.94 (d, 1H), 3.37 (s, 3H), 2.32 (s, 3H), 1.30 (s, 9H).

Similarly, the following 4"-deoxy-4"-acylamido-9(S)-erythromycylamines wherein the acylamido group is identified below are prepared from appropriate 4"-deoxy-4"-acylamidoerythromycin A derivatives. The reaction mixtures of Examples 61–64 are worked up by adding them to water (20 ml.)—ethyl acetate (30 ml.) rather than to water—methylene chloride.

| Example | Z | NMR: $\delta_{CDCL_3}^{TMS}$ |
|---|---|---|
| 61 | CH$_2$-(2-FC$_6$H$_4$) | 7.25 (m, 4H), 6.03 (d, 1H), 3.68 (s, 2H), 3.35 (s, 3H), 2.31 (s, 6H). |
| 62 | CH$_2$-(3-ClC$_6$H$_4$) | 7.33 (m, 4H), 6.08 (d, 1H), 3.63 (s, 2H), 3.36 (s, 3H), 2.33 (s, 6H). |
| 63 | 2-thienyl | 7.61 (m, 2H), 7.15 (m, 1H), 6.36 (d, 1H), 3.40 (s, 3H), 2.36 (s, 6H). |
| 64 | CH$_2$—(3,4-Cl$_2$C$_6$H$_3$) | 7.26 (m, 3H), 6.06 (d, 1H), 3.60 (s, 2H), 3.30 (s, 3H), 2.30 (s, 6H). |

EXAMPLE 65

Following the procedure of Example 61, the compounds of Examples 38, 39, 41, 43–46, 48–56 and 57 are converted to corresponding 4"-deoxy-4"-(Z-substituted)-9(S)-erythromycylamines wherein Z is as defined in said Examples.

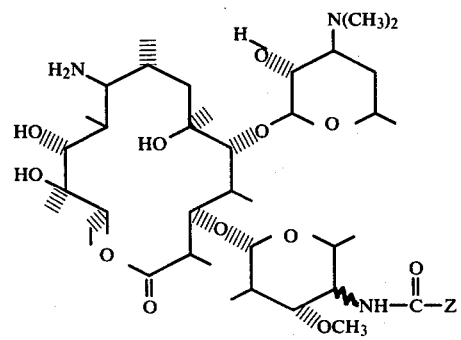

EXAMPLE 66

The compounds tabulated below are prepared from appropriate acyl chlorides and appropriate 4"-deoxy-4"-amino-oleandomycins according to the method of Example 25.

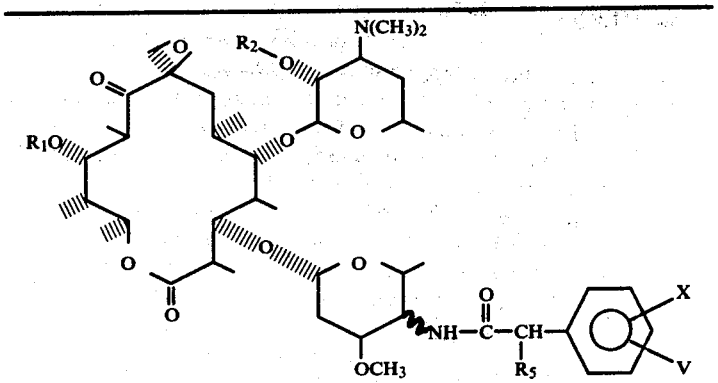

| R₁ | R₂ | R₅ | X | Y |
|---|---|---|---|---|
| Ac | H | NH₂ | H | H |
| Ac | H | NH₂ | 4-Cl | H |
| Ac | H | NH₂ | 4-OCH₃ | H |
| Pr | Pr | NH₂ | H | H |
| Pr | H | NH₂ | 4-t-C₄H₉ | H |
| Pr | H | NH₂ | H | 4-CF₃ |
| H | H | NH₂ | 3-CH₃ | H |
| Ac | H | NH₂ | 4-OH | H |
| Ac | Ac | NH₂ | 2-Br | 4-Br |
| Pr | H | NH₂ | 2-Cl | 4-Cl |
| Pr | H | NH₂ | 4-O-n-C₄H₉ | 3-CH₃ |
| H | H | NH₂ | 3-C₂H₅ | H |
| H | H | NH₂ | 4-F | H |
| H | H | NH₂ | 2-CH₃ | 4-Cl |
| H | H | NH₂ | 2-OC₂H₅ | 6-CH₃ |
| Ac | H | Cl | 3-CH₃ | H |
| Ac | Ac | Cl | 4-O-n-C₃H₇ | H |
| Ac | H | Cl | 4-O-n-C₄H₉ | 3-CH₃ |
| Pr | H | Cl | H | H |
| Pr | Pr | Cl | 3-Cl | H |
| Ac | H | Cl | H | 4-CF₃ |
| Ac | H | Cl | 4-n-C₄H₉ | H |
| H | H | Cl | 3-CH₃ | 4-CH₃ |
| Ac | H | OH | 4-Cl | H |
| Ac | H | OH | 2-Cl | 6-Cl |
| Ac | H | OH | 2-OH | 5-OH |
| Pr | H | OH | 4-OC₂H₅ | H |
| Pr | H | OH | 3-F | H |
| H | H | OH | 2-Br | H |
| H | H | OH | 3-Cl | 4-OCH₃ |
| Ac | Ac | OH | H | 3-CF₃ |
| H | Ac | OH | 3-OCH₃ | 4-OCH₃ |
| H | H | OH | 2-CH₃ | 4-CH₃ |
| Pr | Ac | OH | 4-OH | 3-OCH₃ |
| Ac | H | OH | H | 4-n-C₄H₉ |
| Ac | H | OCH₃ | 3-OH | 4-OCH₃ |
| Ac | H | OCH₃ | 3-CH₃ | 4-CH₃ |
| Ac | Ac | OCH₃ | 4-Br | H |
| Ac | Ac | OCH₃ | H | H |
| H | H | OCH₃ | 4-Cl | H |
| Ac | H | OCH₃ | 3-Cl | 4-Cl |
| Pr | H | OCH₃ | 3-Cl | 4-F |
| Pr | H | OCH₃ | 4-F | H |
| Pr | Pr | OCH₃ | 4-OCH₃ | H |
| H | H | CH₃ | H | H |
| H | Ac | CH₃ | H | 4-Cl |
| H | Pr | CH₃ | H | 2-Cl |
| Ac | H | CH₃ | 2-Cl | 4-Cl |
| Pr | H | CH₃ | 4-OCH₃ | H |
| Ac | Ac | CH₃ | 2-CH₃ | H |
| Pr | Ac | CH₃ | 4-O-n-C₄H₉ | H |
| Ac | H | CH₃ | 4-t-C₄H₉ | H |
| Ac | H | CH₃ | 2-OCH₃ | 4-OCH₃ |
| Ac | Pr | CH₃ | 4-C₂H₅ | H |
| H | H | CH₃ | 4-O-n-C₄H₉ | 3-Cl |
| H | H | CH₃ | 2-OCH₃ | 6-CH₃ |
| Ac | Ac | CH₃ | 2-OH | 3-OH |
| Pr | Pr | CH₃ | 2-Br | H |
| Ac | H | OCH₃ | H | 3-CF₃ |
| H | H | OCH₃ | 3-Cl | 4-CF₃ |
| H | H | OC₂H₅ | H | H |
| H | H | O-n-C₄H₉ | H | H |
| Ac | H | O-n-C₃H₇ | H | H |

-continued

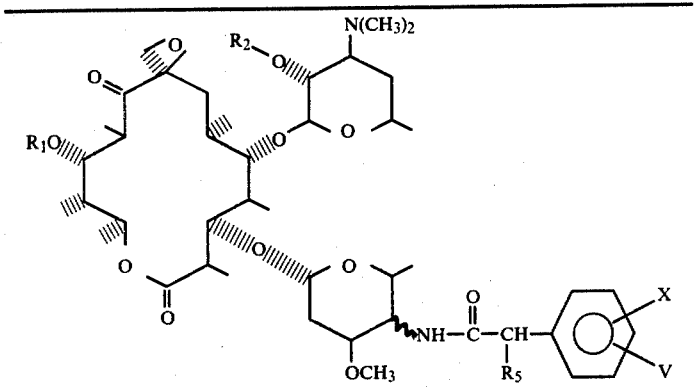

| R₁ | R₂ | R₅ | X | Y |
|---|---|---|---|---|
| Ac | H | O-n-C₄H₉ | 3-Cl | 4-Cl |
| H | H | OC₂H₅ | 3-CH₃ | 4-CH₃ |
| Ac | Ac | OC₂H₅ | 4-Cl | H |
| Ac | Ac | O-n-C₄H₉ | H | 4-Br |
| Ac | H | O-n-C₃H₇ | 3-F | 4-F |
| H | H | OC₂H₅ | 4-t-C₄H₉ | H |
| Pr | H | OCH₃ | 3-OCH₃ | 4-OCH₃ |
| Pr | H | O-n-C₄H₉ | 3-OCH₃ | 4-OCH₃ |
| H | H | OC₂H₅ | H | 4-O-n-C₄H₉ |
| Ac | Ac | O-n-C₃H₇ | 4-C₂H₅ | H |
| Ac | H | OCH₃ | 4-OH | H |
| Pr | Pr | OC₂H₅ | H | 4-CF₃ |
| H | H | O-n-C₄H₉ | H | 4-CF₃ |

EXAMPLE 67

The following compounds are prepared from appropriate acid chlorides or acids and erythromycin derivatives according to the procedures of Examples 1 or 25.

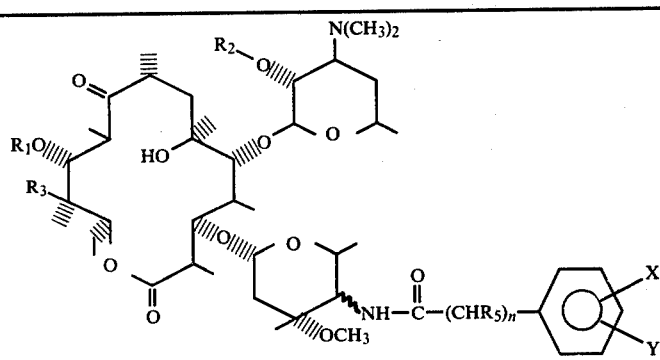

| R₁O | R₃ | R₂ | n | R₅ | X | Y | Method |
|---|---|---|---|---|---|---|---|
| OH | OH | H | 1 | H | 4-O-n-C₄H₉ | H | 1 |
| OH | OH | H | 1 | H | 4-Cl | H | 1 |
| OH | OH | H | 1 | H | 4-Br | H | 1 |
| OH | OH | H | 1 | H | H | 3-CF₃ | 1 |
| OH | OH | H | 1 | H | 2-Cl | 6-Cl | 1 |
| OH | OH | H | 1 | H | 2-F | 4-F | 1 |
| OH | OH | H | 1 | H | 2-Cl | 3-CF₃ | 1 |
| OH | OH | Ac | 1 | H | 2-Br | 5-OCH₃ | 1 |
| OH | OH | Ac | 1 | H | 4-Cl | 2-OH | 1 |
| OH | OH | H | 1 | H | 4-Cl | 2-OCH₃ | 1 |
| OH | OH | Pr | 1 | H | 4-CH₃ | H | 25 |
| OH | OH | Pr | 1 | H | H | 4-t-C₄H₉ | 25 |
| OH | OH | Ac | 1 | H | H | 4-CF₃ | 25 |
| OH | OH | H | 1 | H | 3-CH₃ | 4-CH₃ | 25 |
| OH | H | H | 1 | H | 2-OH | H | 1 |
| OH | H | H | 1 | H | H | 2-CF₃ | 1 |
| OH | H | Ac | 1 | H | 2-CH₃ | 4-OCH₃ | 1 |
| OH | H | Pr | 1 | H | 2-Cl | 3-CF₃ | 1 |
| OH | H | Ac | 1 | H | H | 4-n-C₄H₉ | 25 |
| OH | H | H | 1 | H | 2-Br | 4-Br | 25 |
| OH | OH | H | 1 | Cl | 4-O-n-C₃H₇ | H | 1 |
| OH | OH | H | 1 | Cl | H | 4-CF₃ | 1 |
| OH | OH | H | 1 | Cl | 4-OH | 3-OCH₃ | 1 |
| OH | OH | Ac | 1 | Cl | 3-Cl | H | 25 |

-continued

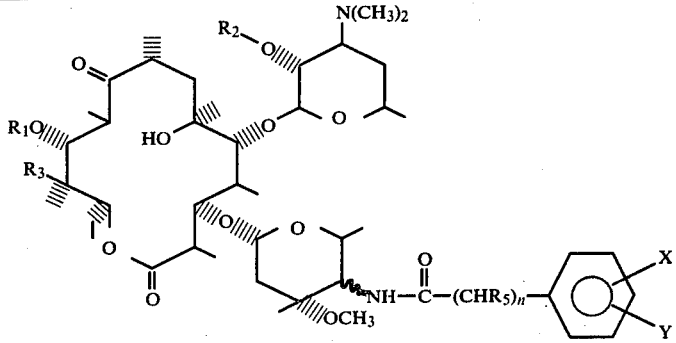

| R₁O | R₃ | R₂ | n | R₅ | X | Y | Method |
|---|---|---|---|---|---|---|---|
| OH | H | H | 1 | Cl | H | H | 1 |
| OH | H | H | 1 | Cl | H | 4-CF₃ | 1 |
| OH | H | Ac | 1 | Cl | H | 2-F | 1 |
| OH | H | Pr | 1 | Cl | 3-CH₃ | 4-CH₃ | 1 |
| —O—C(O)—O— | | H | 1 | H | H | H | 1 |
| —O—C(O)—O— | | H | 1 | H | 2-Cl | H | 1 |
| —O—C(O)—O— | | H | 1 | H | 2-F | H | 1 |
| —O—C(O)—O— | | Ac | 1 | H | 2-OCH₃ | H | 1 |
| —O—C(O)—O— | | H | 1 | H | 2-F | 6-F | 25 |
| —O—C(O)—O— | | Pr | 1 | H | 4-CH₃ | H | 1 |
| —O—C(O)—O— | | Ac | 1 | H | H | 3-CF₃ | 1 |
| —O—C(O)—O— | | H | 1 | H | 3-OCH₃ | 4-OCH₃ | 1 |
| —O—C(O)—O— | | H | 1 | H | 3-Cl | 4-O-n-C₄H₉ | 1 |
| —O—C(O)—O— | | Ac | 1 | Cl | H | H | 1 |
| —O—C(O)—O— | | H | 1 | Cl | H | 2-OCH₃ | 25 |
| —O—C(O)—O— | | H | 1 | Cl | 3-Cl | 4-CF₃ | 1 |
| —O—C(O)—O— | | H | 1 | Cl | 3-OCH₃ | 4-OH | 1 |
| —O—C(O)—O— | | H | 1 | Cl | 2-CH₃ | 4-CH₃ | 25 |
| AcO | OH | H | 1 | OCH₃ | H | H | 1 |
| AcO | OH | H | 1 | OCH₃ | H | 4-Cl | 1 |
| AcO | OH | H | 1 | OCH₃ | H | 4-F | 1 |
| OH | OH | H | 1 | OCH₃ | 3-Cl | 4-Cl | 1 |
| OH | OH | Ac | 1 | OCH₃ | H | 4-OCH₃ | 1 |
| OH | OH | H | 1 | OCH₃ | H | 4-O-n-C₄H₉ | 25 |
| OH | OH | Ac | 1 | OCH₃ | 4-t-C₄H₉ | H | 1 |
| OH | OH | H | 1 | OCH₃ | 3-CH₃ | 4-CH₃ | 1 |
| OH | OH | H | 1 | OCH₃ | H | 4-CF₃ | 25 |
| OH | OH | H | 1 | OCH₃ | 3-Cl | 4-CF₃ | 25 |
| OH | H | H | 1 | OCH₃ | H | H | 1 |
| OH | H | Pr | 1 | OCH₃ | 3-Cl | 4-Cl | 1 |
| AcO | H | H | 1 | OCH₃ | 3-CH₃ | 4-CH₃ | 1 |
| AcO | H | H | 1 | OCH₃ | H | 4-t-C₄H₉ | 25 |
| OH | H | H | 1 | O-n-C₄H₉ | H | H | 1 |
| OH | H | H | 1 | O-n-C₄H₉ | 3-Cl | 4-Cl | 1 |
| OH | OH | Pr | 1 | O-C₂H₅ | H | H | 1 |
| AcO | OH | H | 1 | O-n-C₄H₉ | H | H | 1 |
| OH | OH | H | 1 | O-n-C₃H₇ | H | 4-OCH₃ | 25 |
| PrO | OH | H | 1 | OC₂H₅ | 3-OCH₃ | 4-OCH₃ | 25 |
| OH | H | H | 1 | OC₂H₅ | H | 4-O-n-C₄H₉ | 1 |
| OH | H | H | 1 | CH₃ | H | H | 25 |
| OH | H | H | 1 | CH₃ | 2-F | 6-F | 1 |
| OH | H | H | 1 | CH₃ | 2-Cl | 6-Cl | 1 |
| OH | H | Ac | 1 | CH₃ | H | 4-Br | 25 |
| OH | H | H | 1 | CH₃ | 2-Cl | 4-CF₃ | 1 |
| OH | H | Pr | 1 | CH₃ | 3-C₂H₅ | H | 25 |
| OH | H | H | 1 | CH₃ | 4-n-C₄H₉ | H | 1 |
| OH | H | H | 1 | CH₃ | 3-OC₂H₅ | H | 1 |
| OH | H | H | 1 | CH₃ | 4-O-n-C₄H₉ | H | 1 |
| —O—C(O)—O— | | H | 1 | NH₂ | H | H | 1 |
| —O—C(O)—O— | | Ac | 1 | NH₂ | H | 4-Cl | 1 |
| —O—C(O)—O— | | H | 1 | NH₂ | H | 4-OH | 1 |
| —O—C(O)—O— | | H | 1 | NH₂ | 3-Cl | 4-OH | 1 |
| —O—C(O)—O— | | H | 1 | NH₂ | 2-CH₃ | H | 1 |
| —O—C(O)—O— | | Ac | 1 | NH₂ | 2-OCH₃ | H | 25 |
| —O—C(O)—O— | | H | 1 | NH₂ | 2-OCH₃ | 4-Cl | 25 |
| —O—C(O)—O— | | H | 1 | NH₂ | H | 3-CF₃ | 25 |
| —O—C(O)—O— | | H | 1 | NH₂ | H | 4-t-C₄H₉ | 25 |
| —O—C(O)—O— | | H | 1 | NH₂ | H | 4-Br | 1 |
| —O—C(O)—O— | | H | 1 | OCH₃ | H | H | 1 |
| —O—C(O)—O— | | H | 1 | O-n-C₄H₉ | H | H | 1 |

-continued

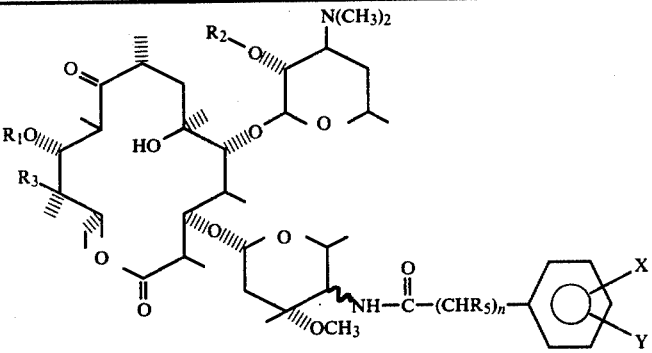

| R₁O | R₃ | R₂ | n | R₅ | X | Y | Method |
|---|---|---|---|---|---|---|---|
| —O—C(O)—O— | H | 1 | OCH₃ | H | 4-CF₃ | 1 | |
| —O—C(O)—O— | Ac | 1 | OC₂H₅ | 3-Cl | 4-Cl | 1 | |
| —O—C(O)—O— | Pr | 1 | OCH₃ | H | 4-F | 1 | |
| —O—C(O)—O— | Ac | 1 | O-n-C₃H₇ | 3-OCH₃ | 4-OCH₃ | 25 | |
| —O—C(O)—O— | H | 1 | OCH₃ | 4-t-C₄H₉ | H | 25 | |
| —O—C(O)—O— | H | 1 | OCH₃ | H | 4-CH₃ | 1 | |
| —O—C(O)—O— | H | 1 | OC₂H₅ | H | 4-O-n-C₃H₇ | 1 | |
| —O—C(O)—O— | H | 1 | OC₂H₅ | H | 4-O-n-C₃H₇ | 1 | |
| —O—C(O)—O— | H | 1 | OCH₃ | H | Br | 25 | |

Note: the table headers actually are: R₁O, R₃, R₂, n, R₅, X, Y, Method

EXAMPLE 68

Repetition of the procedures of Examples 1 or 25 but using the appropriate 11-alkanoyl-4″-deoxy-4″-amino-erythromycin A 6,9-hemiketal and the appropriate acid chloride or acid reactant affords the following compounds:

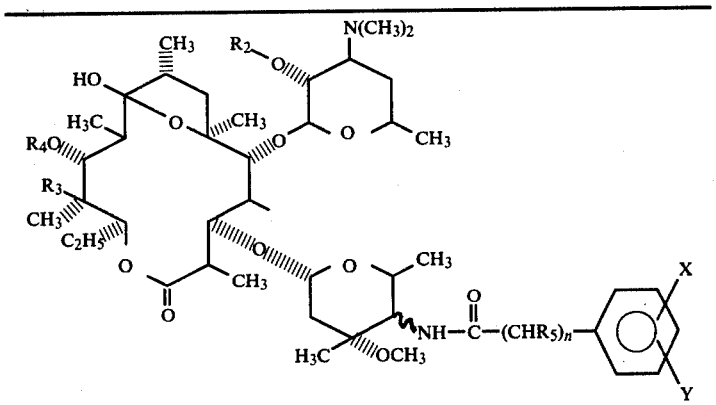

| R₄O | R₃ | R₂ | n | R₅ | X | Y | Method |
|---|---|---|---|---|---|---|---|
| AcO | OH | H | 1 | H | H | H | 1 |
| AcO | OH | H | 1 | H | 2-F | H | 1 |
| AcO | OH | H | 1 | H | 2-OCH₃ | H | 1 |
| AcO | OH | H | 1 | H | 3-Cl | H | 1 |
| PrO | OH | H | 1 | H | 4-Br | H | 25 |
| AcO | OH | H | 1 | H | 4-O-n-C₄H₉ | H | 25 |
| AcO | OH | H | 1 | H | 3-OH | H | 1 |
| AcO | OH | H | 1 | H | 4-t-C₄H₉ | H | 1 |
| PrO | OH | H | 1 | H | H | 4-CF₃ | 1 |
| AcO | OH | H | 1 | H | 2-Cl | 3-CF₃ | 25 |
| AcO | OH | H | 1 | H | 4-Cl | 2-OC₂H₅ | 25 |
| PrO | OH | H | 1 | H | 2-CH₃ | 4-Cl | 1 |
| AcO | OH | H | 1 | H | 2-Cl | 4-Cl | 1 |
| PrO | OH | H | 1 | H | 2-F | 6-F | 1 |
| AcO | OH | Pr | 1 | H | 3-C₂H₅ | H | 25 |
| AcO | OH | Ac | 1 | H | 2-Br | 5-Br | 25 |
| PrO | OH | H | 1 | H | 2-OH | 4-OH | 1 |
| PrO | OH | H | 1 | H | 2-O-n-C₄H₉ | 3-OCH₃ | 1 |
| AcO | OH | Ac | 1 | H | 4-n-C₄H₉ | H | 1 |
| —O—C(O)—O— | H | 1 | H | H | H | 1 | |
| —O—C(O)—O— | H | 1 | H | 2-F | H | 25 | |
| —O—C(O)—O— | H | 1 | H | 2-OCH₃ | H | 1 | |
| —O—C(O)—O— | H | 1 | H | 6-OCH₃ | 2-F | 1 | |
| —O—C(O)—O— | H | 1 | H | 2-Cl | 4-Cl | 1 | |
| —O—C(O)—O— | Ac | 1 | H | 3-C₂H₅ | H | 25 | |
| —O—C(O)—O— | H | 1 | H | 2-O-n-C₄H₉ | 3-OCH₃ | 1 | |

-continued

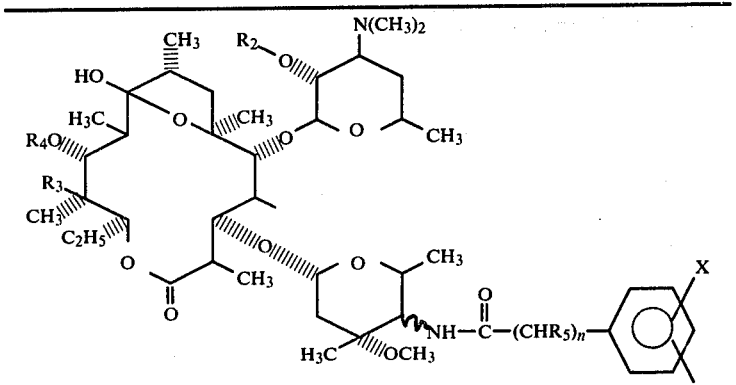

| R4O | R3 | R2 | n | R5 | X | Y | Method |
|---|---|---|---|---|---|---|---|
| —O—C(O)—O— | | Pr | 1 | H | H | 4-n-$C_4H_9$ | 1 |
| —O—C(O)—O— | | H | 1 | H | 2-Cl | 3-$CF_3$ | 1 |

EXAMPLE 69

4"-Deoxy-4"-[4-(1,2,3-thiadiazolyl)carboxamido]oleandomycin

A. To a 25° C. solution of 2'-acetyl-4"-deoxy-4"-amino-oleandomycin (2.0 g., 2.7 mmoles) and triethylamine (0.77 ml., 5.5 mmoles) in dry methylene chloride (20 ml.) is added, with stirring, 1,2,3-thiadiazole-4-carboxylic acid chloride (0.41 g., 2.7 mmoles) in one portion. After 10 minutes, the reaction mixture is stirred methylene chloride (80 ml.) and water (100 ml.), and the pH then adjusted to 9.5 with 1 N aqueous sodium hydroxide. The organic layer is separated, washed four times with equal volumes of water and dried ($Na_2SO_4$). The solvent is removed under reduced pressure to give the crude product as a tan foam (2.5 g.). Silica gel chromatography (200 g. silica gel; 3½ cm.×49 cm. column; 95:5 by volume chloroform:isopropanol elution) yields pure 2'-acetyl-4"-deoxy-4"-[4-(1,2,3-thiadiazolyl)carboxamido]oleandomycin as a colorless, amorphous foam (1.4 g.).

NMR: $\delta_{CDCl_3}^{TMS}$ 3.51 (s, 3H), 2.10 (s, 3H).

B. The 2'-acetyl derivative is stirred for 24 hours at 25° C. in methanol (30 ml.) and the methanol then removed in vacuo to give the title compound as a white amorphous foam (1.3 g., 60.3%).

NMR: $\delta_{CDCl_3}^{TMS}$ 9.25 (s, 1H), 3.50 (s, 3H), 2.32 (s, 6H).

Mass spectrum: m/e=256, 158.

EXAMPLES 70-90

Following the procedure of Example 69, the compounds tabulated were prepared but using the appropriate acid chloride in place of 1,2,3-thiadiazole-4-carboxylic acid chloride.

In those cases where the 2'-acetyl-4"-deoxy-4"-(acylamido)oleandomycin precursor to a given 4"-deoxy-4"-(acylamido)oleandomycin is not reported, the precursor was not isolated prior to deacetylation.

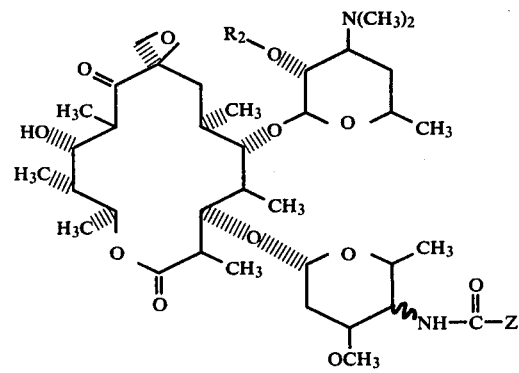

The percent values reported below the Z variable represent the yield of the particular compound calculated on the basis of starting 2'-acetyl-4"-deoxy-4"-amino-oleandomycin.

| Example | R2 | Z | NMR: $\delta_{CDCl_3}^{TMS}$ | Mass Spectrum: m/e |
|---|---|---|---|---|
| 70 | H | 4-pyridyl (61.7%) | AB pattern with $H_A$ at 7.58, $H_A$ at 8.70 ($J_{AB} \simeq 5Hz$, aromatic ring protons), 3.40 (s, 3H), 2.25 (s, 6H). | 249. 158 |
| 71 | H | 2-pyrazinyl | 9.43 (m, 1H), 8.80 (m, 1H), 250, 158 | |
| | | (43.2%) | 8.62 (m, 1H), 3.46 (s, 3H), 2.32 (s, 6H). | |
| 72 | H | 5-isothiazolyl (62.5%) | AB pattern with $H_A$ at 7.52, $H_B$ at 8.42 ($J_{AB}$ = 1Hz, 2H, heterocyclic ring protons), 3.40 (s, 3H), 2.27 (s, 6H). | 255,158 |
| 73 | H | 4-isothiazolyl (27.0%) | 9.16 (s, 1H), 8.84 (s, 1H), 3.41 (s, 3H), 2.27 (s, 6H). | |
| 74 | H | 3-methyl-5-isothiazolyl | 7.30 (s, 1H), 3.40 (s, 3H), | 265,158 |

-continued

| Example | R₂ | Z | NMR: δ $_{CDCl_3}^{TMS}$ | Mass Spectrum: m/e |
|---|---|---|---|---|
| | | (57.2%) | 2.51 (s, 3H), 2.27 (s, 6H). | |
| 75 | COCH₃ | 4-thiazolyl | ($J_{AB} \cong$ 1Hz, 2H, heterocyclic ring protons), AB pattern, H$_A$ at 8.20, H$_B$ at 8.82, 3.45 (s, 3H), 2.27 (s, 6H), 2.09 (s, 3H). | |
| 76 | H | 4-thiazolyl (55.7%) | AB pattern with H$_A$ at 8.19, H$_B$ at 8.79 ($J_{AB} \cong$ 2Hz, 2H, heterocyclic ring protons), 3.41 (s, 3H), 2,28 (s, 6H). | |
| 77 | COCH₃ | 4-methyl-5-thiazolyl | 8.88 (s, 1H), 3.51 (s, 3H), 2.35 (s, 6H), 2.14 (s, 3H). | |
| 78 | H | 4-methyl-5-thiazolyl (68.4%) | 8.82 (s, 1H), 3.52 (s, 3H), 2.86 (s, 3H), 2.40 (s, 6H). | |
| 79 | COCH₃ | 2-methyl-4-thiazolyl | 7.94 (s, 1H), 3.44 (s, 3H), 2.73 (s, 3H), 2.28 (s, 6H), 2.08 (s, 3H). | |
| 80 | H | 2-methyl-4-thiazolyl (41.0%) | 7.95 (s, 1H), 3.45 (s, 3H), 2.75 (s, 3H), 2.30 (s, 6H). | |
| 81 | COCH₃ | 4-methyl-5-oxazolyl | 7.78 (s, 1H), 3.44 (s, 3H), 2.51 (s, 3H), 2.26 (s, 6H), 2.06 (s, 3H). | |
| 82 | H | 4-methyl-5-oxazolyl (79.1%) | 7.80 (s, 1H), 3.43 (s, 3H), 2.52 (s, 3H), 2.29 (s, 6H). | |
| 83 | H | 5-methyl-3-isoxazolyl (60.5%) | 6.44 (s, 1H), 3.43 (s, 3H), 2.50 (s, 3H), 2.31 (s, 6H). | |
| 84 | H | 3-methyl-3-isoxazolyl (52.1%) | 6.69 (s, 1H), 3.39 (s, 3H), 2.35 (s, 3H), 2.30 (s, 6H). | 253,158 |
| 85 | H | 2-furyl | 7.47 (s, 1H), 7.12 (m, 1H), 6.51 (m, 1H), 3.44 (s, 3H), 2.30 (s, 6H). | |
| 86 | H | benzyl | 7.38 (s, 5H), 3.67 (s, 2H), 3.41 (s, 3H), 2.30 (s, 6H). | |
| 87 | Ac | 2-methyl-4-oxazolyl | 8.05 (s, 1H), 2.27 (s, 6H), | |
| 88 | H | 2-methyl-4-oxazolyl | 8.05 (s, 1H), 3.43 (s, 3H), 2.48 (s, 3H), 2.28 (s, 6H). | |
| 89 | H | 3-furyl | 7.91 (s, 1H), 7.40 (s, 1H), 6.63 (s, 1H), 3.41 (s, 3H), 2.45 (s, 6H). | 238,158 |
| 90 | H | 2-pyridyl | 8.60 (m, 1H), 8.20 (m, 1H), 7.85 (m, 1H), 7.42 (m, 1H), 3.45 (s, 3H), 2.30 (s, 6H). | 249,158 |

EXAMPLE 91

4"-Deoxy-4"-nicotinamido-oleandomycin

To a solution of 4"-deoxy-4"-amino-oleandomycin (2.0 g., 2.7 mmoles) in 35 ml. of acetone and 15 ml. of water maintained at pH 7.9–8.0 by addition of 1 N aqueous sodium hydroxide, nicotinoyl chloride hydrochloride (3.12 g., 14.8 mmoles) is added portionwise over approximately one hour. The reaction mixture is then poured into a stirring mixture of 300 ml. ethyl acetate and 300 ml. water; and the pH adjusted to 9.5 with 1 N aqueous sodium hydroxide. The organic layer is separated, washed twice with 300 ml. portions of water and dried over anhydrous sodium sulfate. Solvent removal in vacuo affords crude 2'-acetyl-4"-deoxy-4"-nicotinamido-oleandomycin as a yellow foam. Chromatography on silica gel (initially eluting with chloroform, and finally a 9:1 by volume chloroform/isopropanol mixture) yields 530 mg. of pure amorphous 2'-acetyl-4"-deoxy-4"-nicotinamido-oleandomycin (23.5% yield). Overnight stirring of the entire 530 mg. sample at 25° C. in 25 ml. of methanol followed by in vacuo solvent removal affords the title compound in quantitative yield as a colorless foam.

NMR: $\delta_{CDCl_3}^{TMS}$ 8.66 (m, 1H), 8.05 (m, 1H), 7.39 (m, 1H), 3.41 (s, 3H), 2.64 (s, 6H).

EXAMPLE 92

4"-Deoxy-4"-picolinamido-oleandomycin

To a 25° C. solution of 2"-acetyl-4"-deoxy-4"-amino-oleandomycin (6.0 g., 8.2 mmoles) and 2-picolinic acid (1.10 g., 9.0 mmoles) in 75 ml. of methylene chloride, N,N'-dicyclohexylcarbodiimide (1.80 g., 9.0 mmoles) is added. After 1.5 hours of stirring at 25° C. (during which time, a heavy precipitate of N,N'-dicyclohexylurea forms), additional 2-picolinic acid (1.1 g., 9.0 mmoles) and N,N'-dicyclohexylcarbodiimide (1.8 g., 9.0 mmoles) are added, and the mixture stirred at 25° C. for an additional hour. The reaction mixture is then filtered through diatomaceous earth. The filtrate is stirred with 100 ml. of water while the pH is adjusted to 9.5 with aqueous 1 N sodium hydroxide. The organic layer is separated, washed with two 100 ml. portions of water, dried over anhydrous sodium sulfate, and the solvent removed in vacuo to afford crude 2'-acetyl-4"-deoxy-4"-picolinamido-oleandomycin (10.5 g.). The crude product is stirred at 25° C. overnight in 150 ml. of methanol. Solvent removal in vacuo gives the title product in crude form. Silica gel (150 g.) chromatography, eluting with chloroform initially, and later with chloroform/isopropanol (95:5 by volume) yields 4.5 g. of 4"-deoxy-4"-picolinamido-oleandomycin as a colorless amorphous foam (69.3%). 1.5 g. of the amorphous product is crystallized from ethyl acetate to give crystalline 4''-deoxy-4''-picolinamido-oleandomycin equimolar ethyl acetate solvate, 1.2 g., m.p. 140°–143° C.

NMR: $\delta_{CDCl_3}^{TMS}$ 8.13 (m, 4H), 3.44 (s, 3H), 2.30 (s, 6H), 2.05 (s, 3H).

EXAMPLES 93–97

The procedure of Example 91 is repeated but using the appropriate acid in place of 2-picolinic acid and the appropriate 4''-deoxy-4''-amino-macrolide to produce the following compounds:

93. 2'-acetyl-4''-deoxy-4''-(2-thienyl)carboxamidooleandomycin as a colorless, amorphous foam in 65% yield.

NMR: $\delta_{CDCl_3}^{TMS}$ 7.46 (s, 1H), 7.39 (s, 1H), 699 (m, 1H), 3.40 (s, 3H), 2.25 (s, 6H), 2.06 (s, 3H).

94. 4''-Deoxy-4''-(2-thienyl)carboxamido-oleandomycin.

NMR: $\delta_{CDCl_3}^{TMS}$ 7.49 (m, 3H), 7.04 (m, 3H), 3.43 (s, 3H), 2.29 (s, 6H).

95. 4''-Deoxy-4''-(3-isoxazolyl)carboxamidooleandomycin.

NMR: $\delta_{CDCl_3}^{TMS}$ 2.27 (s, 6H), 3.40 (s, 3H), AB pattern with $H_A$ at 6.72, $H_B$ at 8.37 ($J_{AB}$=1Hz, 2H).

Mass spectrum: m/e 239, 158.

96. 4''-Deoxy-4''-(3-isoxazolyl)carboxamidoerythromycin A as an off-white foam.

NMR: $\delta_{CDCl_3}^{TMS}$ 8.51 (d, 1H), 7.15 (d, 1H), 6.85 (d, 1H), 3.40 (s, 3H), 2.33 (s, 6H), 1.50 (s, 3H).

97. 4''-Deoxy-4''-(picolinamido)erythromycin A as a white crystalline solid; m.p. 150°–156° C. (dec.).

NMR: $\delta_{CDCl_3}^{TMS}$ 7.90 (m, 4H), 3.31 (s, 3H), 2.30 (s, 6H), 1.46 (s, 3H).

EXAMPLE 98

The procedure of Example 69 is followed but using the appropriate reactants; i.e., acid chloride and 2'-alkanoyl-4''-deoxy-4''-amino-oleandomycins to produce the following compounds:

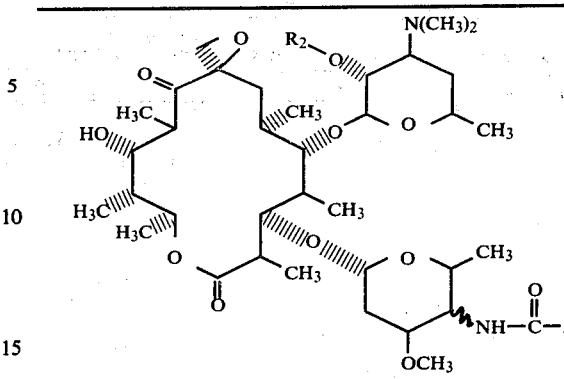

| R₂ | Z | R₂ | Z |
|---|---|---|---|
| Pr | 5-isothiazolyl | Ac | CH₂-(3-methyl-5-isoxazolyl) |
| Pr | 4-isothiazolyl | Pr | CH₂-(4-methyl-5-oxazolyl) |
| Pr | 3-isothiazolyl | Ac | CH₂-(4-methyl-2-thiazolyl) |
| Pr | 4-isothiazolyl | Ac | CH₂-(2-methyl-4-thiazolyl) |
| Ac | 5-methyl-4-isoxazolyl | Pr | CH₂-(3-methyl-5-isothiazolyl) |
| Pr | 3-isoxazolyl | Ac | CH₂-(5-ioxazolyl) |
| Ac | 5-methyl-3-isoxazolyl | Ac | 3-methyl-2-furyl |
| Pr | 5-methyl-3-isoxazolyl | Ac | 5-methyl-3-furyl |
| Pr | 4-(1,2,3-thiadiazolyl) | Pr | 5-methyl-2-thienyl |
| Pr | 2-pyrazinyl | Pr | 5-methyl-3-thienyl |
| Ac | furfuryl | Ac | 2-methyl-4-pyrrolyl |
| Ac | 4-methyl-5-thiazolyl | Pr | 6-methyl-2-pyrazinyl |
| Pr | 4-methyl-5-oxazolyl | Pr | N-methyl-2-pyrrolyl |
| Pr | CH₂-(1-pyrrolyl) | Ac | 1-methyl-4-imidazolyl |

-continued

| R₂ | Z | R₂ | Z |
|---|---|---|---|
| Ac | 4-imidazolyl | Ac | CH₂-(4-pyridyl) |
| Pr | 4-pyridyl | Ac | CH₂-(3-pyridyl) |

Methanolysis of the above tabulated compounds by the procedure of Example 69B affords the corresponding 2'-hydroxy compounds.

EXAMPLE 99

Acid Addition Salts

To a solution of 11-acetyl-4''-deoxy-4''-(2-phenylacetamido)oleandomycin (1.0 mmole) in methanol (50 ml.) or ethyl acetate (50 ml.) is added an equimolar proportion of hydrogen chloride and the reaction mixture stirred at room temperature for one hour. Removal of the solvent by evaporation affords the monohydrochloride salt.

In like manner, the above-named compound and the compounds of Examples 1–98 are converted to their hydrochloride, hydrobromide, sulfate, acetate, butyrate, citrate, glycolate, tartrate, stearate, pamoate, fumarate, gluconate, maleate, p-toluenesulfonate, benzoate and aspartate salts.

When the reactant is an 11,2'-dialkanoyl-4''-deoxy-4''-anilino-oleandomycin, isopropanol rather than methanol is used as solvent.

Repetition of this procedure, but using the erythromycylamine compounds of Examples 60–65 and at least 2 equivalents of the appropriate acid affords the diacid addition salts of said compounds with the acids enumerated above.

EXAMPLE 100

4''-Deoxy-4''-phenylacetamido-oleandomycin phosphate

To a solution of 4''-deoxy-4''-phenylacetamidooleandomycin (6.0 g., 7.5 mmoles) in ethyl acetate is added phosphoric acid (0.79 g., 6.8 mmoles of 85% H₃PO₄) at 0° C. The phosphate salt separates as a crystalline mass and is recovered by filtration and dried.

NMR: $\delta_{CDCl_3}^{TMS}$ 7.33 (s, 5H), 3.66 (s, 2H), 3.36 (s, 3H), 2.89 (s, 6H).

PREPARATION A

11,2'-Diacetyl-4''-deoxy-4''-oxo-oleandomycin

To 4.5 g. of N-chlorosuccinimide, 50 ml. of benzene and 150 ml. of toluene in a dry flask fitted with a magnetic stirrer and nitrogen inlet and cooled to −5° C. is added 3.36 ml. of dimethylsulfide. After stirring at 0° C. for 20 minutes, the contents are cooled to −25° C. and treated with 5.0 g. of 11,2'-diacetyl-oleandomycin in 100 ml. of toluene. Cooling and stirring are continued for 2 hours followed by the addition of 4.73 ml. of triethylamine. The reaction mixture is allowed to stir at 0° C. for 15 minutes, and is subsequently poured into 500 ml. of water. The pH is adjusted to 9.5 with 1 N aqueous sodium hydroxide and the organic layer separated, washed with water and a brine solution and dried over sodium sulfate. Removal of the solvent in vacuo gives 4.9 g. of the desired product as a foam.

NMR (60 MHz) $\delta_{CDCl_3}^{TMS}$ (ppm): 3.48 (s, 3H), 2.61 (m, 2H), 2.23 (s, 2H), and 2.03 (s, 6H).

In like manner, the following 11,2'-dialkanoyl-4"-deoxy-4"-oxo-oleandomycins are prepared from the corresponding 11,2'-dialkanoyl-oleandomycins:
  11,2'-dipropionyl-
  11-acetyl-2'-propionyl-
  11-propionyl-2'-acetyl-

PREPARATION B

11-Acetyl-4"-deoxy-4"-oxo-oleandomycin

A solution of 4.0 g. of 11,2'-diacetyl-4"-deoxy-4"-oxo-oleandomycin in 75 ml. of methanol is allowed to stir at room temperature overnight. The reaction mixture is concentrated under reduced pressure to give the product as a foam. A diethyl ether solution of the residue, on treatment with hexane, gives 2.6 g. of the product as a white solid, m.p. 112°–117° C.

NMR (60 MHz) $\delta_{CDCl_3}^{TMS}$ (ppm): 3.43 (s, 3H), 2.60 (m, 2H), 2.23 (s, 6H), and 2.01 (s, 3H).

Following the above procedures, 11-propionyl-4"-deoxy-4"-oleandomycin is prepared from 11,2'-dipropionyl-4"-deoxy-4"-oxo-oleandomycin.

PREPARATION C

2'-Acetyl-4"-deoxy-4"-oxo-oleandomycin

Dimethylsulfide (0.337 ml.) is added to a turbid solution of 467 mg. of N-chlorosuccinimide in 20 ml. of toluene and 6 ml. of benzene cooled to −5° C. and maintained under a nitrogen atmosphere. After stirring at 0° C. for 20 minutes the mixture is cooled to −25° C. and 1.46 g. of 2'-acetyl-oleandomycin and 15 ml. of toluene are added. Stirring is continued for 2 hours at −20° C. followed by the addition of 0.46 ml. of triethylamine. The reaction mixture is maintained at −20° C. for an additional 5 minutes and then allowed to warm to 0° C. The mixture is poured, with stirring, into 50 ml. of water and 50 ml. of ethyl acetate. The pH of the aqueous mixture is adjusted to 9.5 by addition of aqueous sodium hydroxide solution. The organic layer is subsequently separated, dried over sodium sulfate and concentrated in vacuo to a white foam (1.5 g.). Trituration with diethyl ether gives 864 mg. of crude product, which on recrystallization twice from methylene chloride—diethyl ether gives 212 mg. of the pure product, m.p. 183°–185.5° C.

Analysis: Calc'd for $C_{37}H_{61}O_{13}N$: C, 61.1; H, 8.5; N, 1.9. Found: C, 60.9; H, 8.4; N, 1.9.

NMR (60 MHz) $\delta_{CDCl_3}^{TMS}$ (ppm): 5.60 (m, 1H), 3.50 (s, 3H), 2.73 (m, 2H), 2.23 (s, 6H), and 2.03 (s, 3H).

In like manner, 2'-propionyl-4"-deoxy-4"-oxo-oleandomycin is prepared from 2'-propionyl-oleandomycin.

PREPARATION D

4"-Deoxy-4"-oxo-oleandomycin

A solution of 1.0 g. of 2'-acetyl-4"-deoxy-4"-oxo-oleandomycin in 20 ml. of methanol is allowed to stir at room temperature overnight. The solution is concentrated in vacuo to give the desired product as a white foam, 937 mg.

NMR (60 MHz) $\delta_{CDCl_3}^{TMS}$ (ppm): 5.60 (m, 1H), 3.50 (s, 3H), 2.85 (m, 2H), and 2.26(s, 6H).

Similarly, 2'-propionyl-4"-deoxy-4"-oxo-oleandomycin is hydrolyzed to 4"-deoxy-4"-oxo-oleandomycin.

PREPARATION E

11-Acetyl-4"-deoxy-4"-amino-oleandomycin

To a suspension of 10% palladium-on-charcoal (10 g.) in methanol (100 ml.) is added ammonium acetate (21.2 g.) and the resulting slurry is treated with a solution of 11-acetyl-4"-deoxy-4"-oxo-oleandomycin (20 g.) in 100 ml. of the same solvent. The suspension is shaken at room temperature in a hydrogen atmosphere at an initial pressure of 50 psi. After 1.5 hours, the catalyst is filtered and the filtrate is added with stirring to a mixture of water (1200 ml.) and chloroform (500 ml.). The pH is adjusted from 6.4 to 4.5 and the organic layer is separated. The aqueous layer, after a further extraction with chloroform (500 ml.), is treated with ethyl acetate (500 ml.) and the pH adjusted to 9.5 with 1 N sodium hydroxide. The ethyl acetate layer is separated and the aqueous layer extracted again with ethyl acetate. The ethyl acetate extracts are combined, dried over sodium sulfate and concentrated to a yellow foam (18.6 g.), which on crystallization from diisopropyl ether, provides 6.85 g. of purified product, m.p. 157.5°–160° C., shown by NMR data and thin layer chromatography (TLC) to be a single epimer at the C-4" position. The TLC system used is $CHCl_3$:$CH_3OH$:$NH_4OH$ (9:2:0.1) on silicagel plates. The developing system vanillin:$H_3PO_4$:$C_2H_5OH$ (5 g.: 50 ml.:100 ml.) is sprayed on the TLC plates heated to about 80°–100° C. The major epimer is less polar than is the minor epimer.

NMR ($\delta$, $CDCl_3$): 3.41 (3H)s, 2.70 (2H)m, 2.36 (6H)s, and 2.10 (3H)s.

The other epimer, which exists in the crude foam to the extent of 20–25%, is obtained by gradual concentration and filtration of the mother liquors.

In like manner, the following mono-alkanoyl and dialkanoyl esters of 4"-deoxy-4"-amino-oleandomycin (both C-4" epimers) are prepared from the appropriate monoalkanoyl and di-alkanoyl 4"-deoxy-4"-oxo-oleandomycins. When a 2'-ester is prepared, isopropanol is used as solvent.
  11,2'-diacetyl-
  2'-acetyl
  2'-propionyl-
  11,2'-dipropionyl-
  11-propionyl-
  11-acetyl-2'-propionyl-
  11-propionyl-2"-acetyl-

PREPARATION F

4"-Deoxy-4"-amino-oleandomycin

A solution of 2'-acetyl-4"-deoxy-4"-oxo-oleandomycin (20 g.) in methanol (125 ml.), after stirring at room temperature overnight, is treated with ammonium acetate (21.2 g.). The resulting solution is cooled in an ice bath and treated with sodium cyanoborohydride (1.26 g.). The cooling bath is then removed and the reaction mixture allowed to stir at room temperature for 2 hours. The reaction is poured into water (600 ml.) and diethyl ether (600 ml.) and the pH adjusted from 8.3 to 7.5. The ether layer is separated and the pH of the aqueous adjusted to 8.25. The diethyl ether and ethyl acetate extracts made at this pH are also set aside, and the pH raised to 9.9. The diethyl ether and ethyl acetate extracts at this pH are combined, washed successively with water (1x) and a saturated brine solution and dried over sodium sulfate. The latter extracts, taken at pH 9.9, are connected to a foam and chromatographed on silica gel (160 g.), using chloroform as the loading solvent and initial eluate. After eleven fractions, 12 ml. per fraction are taken, the eluate is changed to 5% methanol--95% chloroform. At fraction 370 the eluate is changed to 10% methanol—90% chloroform and at fraction 440, 15% methanol—85% chloroform is used. Fractions 85–260 are combined and concentrated in vacuo to dryness to provide 2.44 g. of the desired product.

NMR ($\delta$, CDCl$_3$): 5.56 (m, 1H), 3.36 (s, 3H), 2.9 (m, 2H) and 2.26 (s, 6H).

PREPARATION G

2'-Acetyl-4"-deoxy-4"-oxo-erythromycin A

To 3 ml. of methylene chloride and 0.328 ml. of dimethylsulfoxide cooled to about −65° C. and maintained under a nitrogen atmosphere is added 0.652 ml. of trifluoroacetic anhydride. After about a minute a white slurry forms indicating the presence of the trifluoroacetic anhydride--dimethylsulfoxide complex. The the resulting slurry is added dropwise a solution of 1.0 g. of 2'-acetylerythromycin A ethyl acetate, obtained by recrystallization of 2'-acetylerythromycin A from ethyl acetate, in 7 ml. of methylene chloride keeping the temperature at about −65° C. The resulting mixture is allowed to stir for 15 min. at about −60° C. and is then cooled to −70° C. Triethylamine (1.61 ml.) is added rapidly to the reaction mixture and the cooling bath is removed. After stirring for 15 minutes the solution is added to 10 ml. of water and the pH of the aqueous phase adjusted to 10. The organic phase is separated, washed successively with water (3×10 ml.) and brine solution (1×10) and dried over sodium sulfate. Removal of the solvent under reduced pressure gives 929 mg. of the crude product. Recrystallization from methylene chloride—hexane gives 320 mg. of the purified product, m.p. 105°–108° C.

NMR ($\delta$, CDCl$_3$):3.28 (s, 3H), 2.21 (s, 6H), and 2.03 (s, 3H).

In a similar manner, starting with 2'-propionylerythromycin A ethyl acetate and following the above procedure gives 2'-propionyl-4"-deoxy-4"-oxo-erythromycin A.

PREPARATION H

4"-Deoxy-4"-oxo-erythromycin A

A solution of 4.0 g. of 2'-acetyl-4"-deoxy-4"-oxoertythromycin A in 75 ml. of methanol is allowed to stir at ambient temperature for 20 hours. The solvent is removed in vacuo and the residual white foam recrystallized from methylene chloride—hexane, 3.44 g., m.p. 170.5°–172.5° C.

NMR ($\delta$, CDCl$_3$); 3.36 (s, 3H) and 2.33 (s, 6H).

PREPARATION I

4"-Deoxy-4"-amino-erythromycin A

Method (a)

To a stirring solution of 3.0 g. of 4"-deoxy-4"-oxoerythromycin A in 30 ml. of methanol under a nitrogen atmosphere is added 3.16 g. of dry ammonium acetate. After 5 minutes 188 mg. of sodium cyanoborohydride is washed into the reaction mixture with 5 ml. of methanol and the reaction allowed to stir at room temperature overnight. The light yellow solution is poured into 300 ml. of water and the pH adjusted to 6.0. The aqueous is extracted at pH 6, 7, 7.5, 8, 9 and 10 using 125 ml. of diethyl ether for each extraction. The extracts at pH 8, 9 and 10 are combined and washed with 125 ml. of fresh water. The separated aqueous layer is extracted with ether (1×100 ml.) at pH 7, ethyl acetate (1×100 ml.) at pH 7, ether (1×100 ml.) at pH 7.5, ethyl acetate (1×100 ml.) at pH 7.5 and ethyl acetate (1×100 ml.) at pH 8, 9 and 10. The ethyl acetate extracts at pH 9 and 10 are combined, washed with a saturated brine solution and dried over sodium sulfate. Removal of the solvent in vacuo gives 30 mg. of an epimeric mixture of the desired product as an ivory colored foam.

Similarly, 4"-deoxy-4"-amino-erythromycin B is prepared from 4"-deoxy-4"-oxo-erythromycin B.

Method (b)

Twenty grams of 4"-deoxy-4"-oxo-erythromycin A, 31.6 g. of ammonium acetate and 10 g. of 10% palladium-on-charcoal in 200 ml. of methanol is shaken at ambient temperatures in a hydrogen atmosphere at an initial pressure of 50 psi overnight. The spent catalyst is filtered and the filtrate concentrated to dryness in vacuo. The residue is partitioned between water-chloroform at a pH of 5.5. The aqueous layer is separated, the pH adjusted to 9.6 and chloroform adeed. The organic layer is separated, dried over sodium sulfate and concentrated under reduced pressure to dryness. The residual white foam (19 g.) is triturated with 150 ml. of diethyl ether at room temperature for 30 minutes. The resulting solids are filtered and dried to give 9.45 g. of a single epimer indistinguishable from that in Preparation J.

The diethyl ether filtrate is concentrated to dryness to give 6.89 g. of product consisting of the other epimer plus some impurities.

Method (c)

Two grams of 4"-deoxy-4"-oxo-erythromycin A, 3.1 g. of ammonium acetate and 2.0 g. of Raney nickel in 50 ml. of methanol is shaken at room temperature in a hydrogen atmosphere at an initial pressure of 50 psi overnight. An additional 3.16 g. of ammonium acetate and 2.0 g. of Raney nickel are added and the hydrogenation continued for an additional 5 hours. The solids are filtered and the filtrate concentrated to dryness in vacuo. The residue is added with stirring to a mixture of water-chloroform, and the pH adjusted from 6.4 to 5.5. The aqueous phase is separated, the pH adjusted to 9.6 and fresh chloroform added. The chloroform extract is separated, dried over sodium sulfate and concentrated under reduced pressure to give 1.02 g. of the product as a yellow foam. The predominant isomer has the opposite configuration at 4" as the compound of Preparation J.

PREPARATION J

4"-Deoxy-4"-amino-erythromycin A (single epimer)

A solution of 10.0 g. of the epimeric mixture of 2'-acetyl-4"-deoxy-4"-amino-erythromycin A in 150 ml. of methanol is allowed to stir at room temperature under nitrogen for 72 hours. The solvent is removed in vacuo and the residue is dissolved in a stirring mixture of 150 ml. of water and 200 ml. of chloroform. The aqueous layer is discarded and 150 ml. of fresh water is added. The pH of the aqueous layer is adjusted to 5 and the chloroform layer is separated. The pH of the aqueous phase is subsequently adjusted to 5.5, 6, 7, 8 and 9, being extracted after each adjustment with 100 ml. of fresh chloroform. The chloroform extracts from pH 6, 7 and 8 are combined, washed successively with water and dried over sodium sulfate. Removal of the solvent under reduced pressure gives 2.9 g. of an epimeric mixture of 4''-deoxy-4''-amino-erythromycin A. A 1.9 g. sample of the mixture is triturated with diethyl ether causing some of the undissolved foam to crystallize. The solids are filtered and dried to give 67 mg. of a single epimer of 4''-deoxy-4''-amino-erythromycin A, m.p. 140°–147° C.

PREPARATION K 11,2'-Diacetyl-4''-deoxy-4''-oxo-erythromycin A 6,9-hemiketal

A solution of 10 g. of 2'-acetyl-4''-deoxy-4''-oxo-erythromycin erythromycin A in 250 ml. of pyridine is treated with 40 ml. of acetic anhydride and the resulting reaction mixture allowed to stand at room temperature for 10 days. The bulk of the solvent is removed in vacuo and the remaining concentrate added to a mixture of 150 ml. of water and 100 ml. of chloroform. The pH of the aqueous is raised to 9.0 and the chloroform separated, dried over sodium sulfate and concentrated to dryness.

NMR (δ, CDCl$_3$): 3.33 (s, 3H), 2.26 (s, 6H), 2.10 (s, 3H), 2.03 (s, 3H) and 1.55 (s, 3H).

In like manner, but starting with the appropriate 4''-deoxy-4''-oxo-erythromycin A and requisite alkanoic anhydride, the following compounds are synthesized:

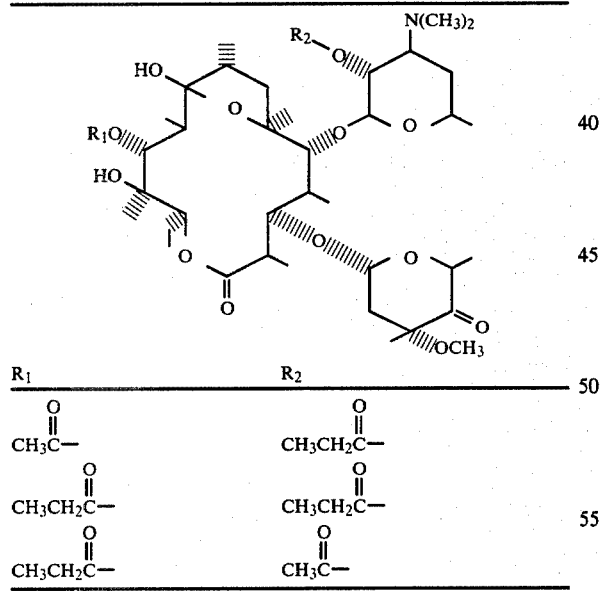

| R$_1$ | R$_2$ |
|---|---|
| CH$_3$C(=O)— | CH$_3$CH$_2$C(=O)— |
| CH$_3$CH$_2$C(=O)— | CH$_3$CH$_2$C(=O)— |
| CH$_3$CH$_2$C(=O)— | CH$_3$C(=O)— |

PREPARATION L

11-Acetyl-4''-deoxy-4''-oxo-erythromycin A 6,9-hemiketal

A solution of 3.0 g. of 11,2'-diacetyl-4''-deoxy-4''-oxo-erythromycin A 9,6-hemiketal in 50 ml. of methanol is allowed to stir under a nitrogen atmosphere overnight. The solvent is removed in vacuo to give the desired product (3.0 g.) as a yellow foam.

NMR (δ, CDCl$_3$): 3.35 (s, 3H), 2.31 (s, 6H), 2.13 (3H) and 1.55 (s, 3H).

In a similar manner, the compounds listed in Preparation K are converted by the above procedure to 11-acetyl-4'''-deoxy-4''-oxo-erythromycin A 6,9-hemiketal and 11-propionyl-4''-deoxy-4''-oxo-erythromycin A 6,9-hemiketal.

PREPARATION M

11-Acetyl-4''-deoxy-4''-amino-erythromycin A 6,9-hemiketal

To a stirred solution of 4.4 g. of 11-acetyl-4''-deoxy-4''-oxo-erythromycin A 6,9-hemiketal and 4.38 g. of ammonium acetate in 75 ml. of methanol is added 305 mg. of 85% sodium cyanoborohydride. After stirring at room temperature overnight, the reaction mixture is poured into 300 ml. of water to which is then added 250 ml. of chloroform. The pH of the aqueous layer is adjusted to 9.8 and the chloroform layer separated. The aqueous layer is extracted with chloroform again, and the chloroform extracts are combined, dried over sodium sulfate and concentrated to a white foam. The residual foam is dissolved in a stirring mixture of 125 ml. of water and 125 ml. of fresh chloroform and the pH adjusted to 4.9. The chloroform is separated and discarded, and the aqueous layer adjusted to pH 5, 6, 7 and 8, being extracted after each adjustment with fresh chloroform. The extracts from the aqueous at pH 6 and 7 are combined, washed with a saturated brine solution and dried over sodium sulfate. Removal of the solvent provides 1.72 g. of the desired product as a white foam. The product is dissolved in a minimal amount of diethyl ether and is subsequently treated with hexane to turbidity. The crystalline product which forms is filtered and dried, 1.33 g., m.p. 204.5°–206.5° C.

NMR (δ, CDCl$_3$): 3.31 (s, 2H), 3.28 (s, 1H), 2.31 (s, 6H), 2.11 (s, 3H) and 1.5 (s, 3H).

Similarly, but starting with the appropriate 4''-deoxy-4''-oxo-erythromycin A and substituting isopropanol for methanol as the reaction solvent affords the following compounds:

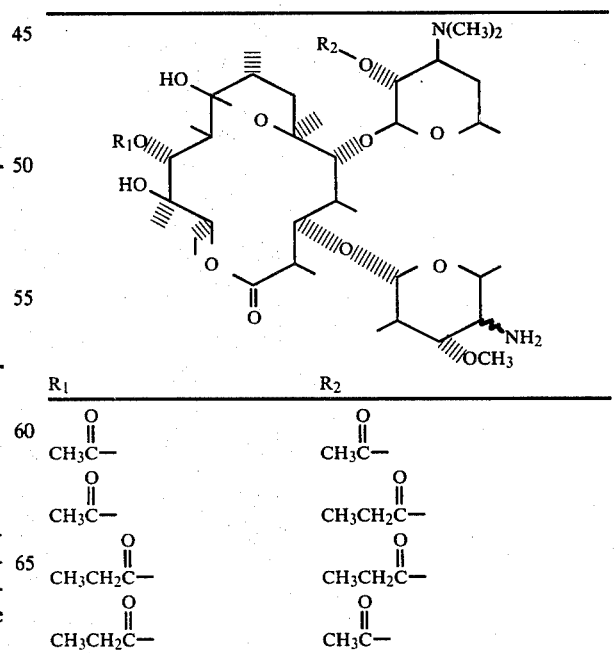

| R$_1$ | R$_2$ |
|---|---|
| CH$_3$C(=O)— | CH$_3$C(=O)— |
| CH$_3$C(=O)— | CH$_3$CH$_2$C(=O)— |
| CH$_3$CH$_2$C(=O)— | CH$_3$CH$_2$C(=O)— |
| CH$_3$CH$_2$C(=O)— | CH$_3$C(=O)— |

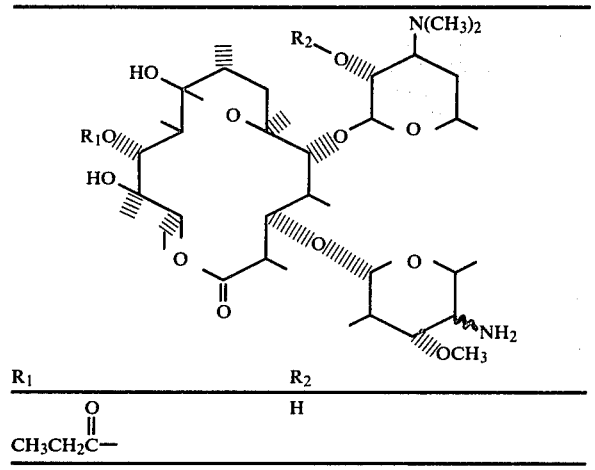

| R₁ | R₂ |
|---|---|
| CH₃CH₂C(=O)— | H |

PREPARATION N

2'-Acetylerythromycin A 6,9-hemiketal 11,12-carbonate ester

To a solution of 13.2 g. of erythromycin A 6,9-hemiketal 11,12-carbonate ester (U.S. Pat. No. 3,417,077) in 150 ml. of benzene is added 1.8 ml. of acetic anhydride, and the reaction mixture allowed to stir at room temperature for 1.5 hours. The solution is poured into 200 ml. of water and the aqueous phase basified to pH 9.0. The benzene layer is separated, dried over sodium sulfate and concentrated in vacuo to 15.3 g. of a white foam. On trituration with 50 ml. of diethyl ether the foam crystallizes. Filtration and drying of the product gives 12.6 g. of pure product, m.p. 224.5°–228.5° C.

NMR ($\delta$, CDCl$_3$): 3.36 (s, 3H), 2.30 (s, 6H), 2.06 (s, 3H) and 1.61 (s, 3H).

In a similar manner, by substituting an equivalent amount of propionic anhydride for acetic anhydride in the above procedure, propionyl-erythromycin A 6,9-hemiketal 11,12-carbonate ester is prepared.

PREPARATION O

2'-Acetyl-4''-deoxy-4''-oxo-erythromycin A 6,9-Hemiketal 11,12-Carbonate Ester

To a suspension of 6.19 g. of N-chlorosuccinimide in 150 ml. of toluene and 50 ml. of benzene cooled to −5° C. is added 4.46 ml. of dimethylsulfide. After stirring for 20 minutes the resulting suspension is cooled to −25° C. and 12.4 g. of 2'-acetylerythromycin A 6,9-hemiketal 11,12-carbonate ester, partially dissolved in 80 ml. of toluene, is added dropwise. The temperature, which is maintained between −19° C. to −25° C. during the addition, is kept at −25° C. for 2 hours. At the end of this period 6.79 ml. of triethylamine is added all at once. The cooling bath is removed and the temperature allowed to rise to −10° C. The reaction mixture is then poured into water and the aqueous phase adjusted from 8.4 to 9.0. The organic layer is separated, dried over sodium sulfate and concentrated under vacuum to a white foam (14.0 g.). Trituration of the residue with diethyl ether causes the foam to crystallize. Filtration and drying of the product gives 11.3 g. of crystalline material, m.p. 212°–213.5° C.

NMR ($\delta$, CDCl$_3$): 5.26 (t, 1H), 3.36 (s, 3H), 2.30 (s, 6H), 2.13 (s, 3H), 1.63 (s, 3H), and 1.50 (s, 3H).

Similarly, 2'-propionyl-4''-deoxy-4''-oxo-erythromycin A 6,9-hemiketal 11,12-carbonate ester is prepared by replacement of the 2'-acetyl ester with an equivalent amount of 2''-propionylerythromycin A 6,9-hemiketal 11,12-carbonate ester.

PREPARATION P

4''-Deoxy-4''-oxo-erythromycin A 6,9-Hemiketal 11,12-Carbonate Ester

Forty-two and nine-tenths grams of 2'-acetyl-4''-deoxy-4''-oxo-erythromycin A 6,9-hemiketal 11,12-carbonate ester is added to 800 ml. of methanol and the resulting solution allowed to stir at room temperature for 72 hours. On removal of the solvent in vacuo there remains 41 g. of the product as a white foam. The residual material is dissolved in about 100 ml. of acetone followed by the careful addition of water to the precipitation point. The resulting crystalline solid is allowed to stir for 40 minutes, and this then filtered and dried to give 34.2 g. of the desired product, m.p. 186.5°–188° C.

NMR ($\delta$, CDCl$_3$): 5.66 (t, 1H), 3.35 (s, 3H), 2.35 (s, 6H), 1.65 (s, 3H) and 1.51 (s, 3H).

PREPARATION Q

4''-Deoxy-4''-amino-erythromycin A 6,9-Hemiketal 11,12-Carbonate Ester

To 189 g. of 4''-deoxy-4''-oxo-erythromycin A 6,9-hemiketal 11,12-carbonate ester in 1200 ml. of methanol at room temperature is added with stirring 193 g. of ammonium acetate. After 5 minutes the resulting solution is cooled to about −5° C. and is subsequently treated with 13.4 g. of 85% sodium cyanoborohydride in 200 ml. of methanol over a 45 minute addition period. The cooling bath is removed and the reaction mixture allowed to stir at room temperature overnight. The reaction mixture is reduced in volume to 800 ml. in vacuo and added to a stirring mixture of 1800 ml. of water and 900 ml. of chloroform. The pH is adjusted from 6.2 to 4.3 with 6 N hydrochloric acid and the chloroform layer separated. The chloroform is combined with 1 l. of water and the pH adjusted to 9.5. The organic phase is separated, dried over sodium sulfate and concentrated under reduced pressure to give 174 g. of a white foam. The residual material is dissolved in a mixture of 1 l. of water and 500 ml. of ethyl acetate and the pH adjusted to 5.5. The ethyl acetate layer is separated and the aqueous layer adjusted to pH 5.7 and 9.5 successively, being extracted after each pH adjustment with 500 ml. of fresh ethyl acetate. The ethyl acetate extract at pH 9.5 is dried over sodium sulfate and concentrated in vacuo to dryness, 130 g. One hundred and twenty grams of the residual foam is dissolved in a mixture of 1 l. of water and 1 l. of methylene chloride. The pH of the aqueous layer is adjusted to 4.4, 4.9 and 9.4 successively, being extracted after each adjustment with 1 l. of fresh methylene chloride. The methylene chloride extract at pH 9.4 is dried over sodium sulfate and concentrated under reduced pressure to give 32 g. of the product as a white foam. Crystallization from 250 ml. of acetone-water (1:1, v:v) gives 28.5 g. of the crystalline epimers.

NMR 100 Mz ($\delta$, CDCl$_3$): 5.20 (1H)m, 3.37 (1.5H)s, 3.34 (1.5H)s, 2.36 (6H)s, 1.66 (3H)s and 1.41 (3H)s.

PREPARATION R

Separation of the Epimers of 4''-Deoxy-4''-amino-erythromycin A 6,9-Hemiketal 11,12-Carbonate Ester Onto a high-pressure-liquid-chromatography column (1.2"×9 cm.) packed with Gf 254 silica gel impregnated with formamide and eluted with chloroform is applied 200 mg. A pressure of 240 psi is applied with a rate of 4.76 cc. per minute and a fraction size of 10 ml. is employed. Fractions 14 through 21 and 24 through 36 are collected.

Fractions 14 through 21 are combined and concentrated to about 50 ml. Water (50 ml.) is added and the pH adjusted to 9.0. The chloroform layer is separated, dried over sodium sulfate and concentrated to give 106 mg. of a white foam. Trituration with diethyl ether causes the foam to crystallize. After stirring at room temperature for one hour the crystalline product is filtered and dried, 31.7 mg., m.p. 194°–196° C.

NMR 100 Mz ($\delta$, CDCl$_3$): 5.24 (1H)d, 5.00 (1H)t, 3.40 (3H)s, 2.40 (6H)s, 1.66 (3H)s, and 1.40 (3H)s.

Fractions 24 through 36 are combined and worked up as above to give 47.1 mg. of product as a white foam, which is identical to the material obtained from the epimeric mixture of Preparation Q by recrystallization from hot acetone-water (1 gm. per 25 ml. water, 20 ml. acetone); NMR data indicate it to be a single epimer.

NMR 100 Mz ($\delta$, CDCl$_3$): 5.12 (1H)d, 3.30 (3H)s, 2.30 (6H)s, 1.62 (3H)s, 1.36 (3H)s.

PREPARATION S

Epimeric 2'-Acetyl-4''-deoxy-4''-aminoerythromycin A 11,12-carbonate Ester and Its 6,9-Hemiketal To a suspension of 11.1 g. of 2'-acetyl-4''-deoxy-4''-oxo-erythromycin A 6,9-hemiketal 11,12-carbonate ester in 300 ml. of isopropanol at room temperature is added with stirring 10.7 g. of ammonium acetate. After 5 minutes 747 mg. of sodium cyanoborohydride in 130 ml. of isopropanol is added over a period of 30 minutes and the resulting reaction mixture is allowed to stir at room temperature overnight. The pale yellow solution is poured into 1100 ml. of water to which is then added 400 ml. of diethyl ether. The pH is adjusted to 4.5 and the ether layer is separated. The aqueous layer is basified to pH 9.5 and extracted (2×500 ml.) with chloroform. The chloroform extracts are combined, dried over sodium sulfate and concentrated to give 7.5 g. of a yellow foam. Recrystallization of the residual material from diethyl ether gives 1.69 g. which is retained along with the mother liquors.

The mother liquor is treated with 75 ml. of water, and the pH adjusted to 5.0. The ether layer is replaced with 75 ml. of fresh ether and the pH adjusted to 5.4. The ether is replaced with ethyl acetate and the pH raised to 10. The basified aqueous layer is extracted (2×75 ml.) with ethyl acetate and the first ethyl acetate extract dried over sodium sulfate and concentrated to dryness. The residual foam (1.96 g.) is added to a mixture of 75 ml. of water and 50 ml. of diethyl ether and the pH adjusted to 5.05. The ether is separated and the aqueous layer adjusted successively to pH 5.4, 6.0, 7.05, and 8.0, being extracted after each pH adjustment with 50 ml. of fresh diethyl ether. The pH is finally adjusted to 9.7 and the aqueous layer extracted with 50 ml. of ethyl acetate. The ether extract carried out at pH 6.0 is combined with 75 ml. of water and the pH adjusted to 9.7. The ether layer is separated, dried and concentrated in vacuo to give 460 mg. of a white foam.

NMR 100 Mz ($\delta$, CDCl$_3$): 5.20 (1H)t, 3.43 (2H)s, 3.40 (1H)s, 2.38 (6H)s, 2.16 (3H)s, 1.70 (3H)s, and 1.54 (3H).

The NMR data indicate the product to be the epimers of 2'-acetyl-4''-deoxy-4''-amino-erythromycin A 6,9-hemiketal 11,12-carbonate ester.

The 1.69 g. indicated above is dissolved in a mixture of 75 ml. of water and 75 ml. of diethyl ether and the pH adjusted to 4.7. The ether is separated and the aqueous layer further extracted with fresh ether (75 ml.) at pH 5.05 and 5.4, and with ethyl acetate (2×75 ml.) at pH 9.7. The combined ethyl acetate extracts are dried over sodium sulfate and concentrated under reduced pressure to give 1.26 g. of a white foam. Crystallization of this residual material gives 411 mg. of product, m.p. 193°–196° C. (dec.). The mother liquor is concentrated to dryness, and the residue dissolved in hot ethyl acetate. The solution is allowed to stand overnight at room temperature. The crystalline solids which precipitate are filtered and dried, 182 mg., m.p. 198°–202° C. (dec.) to give additional product.

NMR 100 Mz ($\delta$, CDCl$_3$): 5.10 (1H)t, 3.34 (2H)s, 3.30 (1H)s, 2.30 (6H)s, 2.08 (3H)s, 1.62 (3H)s, and 1.48 (3H)s.

The NMR data indicate the product to be the epimers of 2'-acetyl-4''-deoxy-4''-amino-erythromycin A 11,12-carbonate ester.

In a similar manner, but starting with 2'-propionyl-4''-deoxy-4''-oxo-erythromycin A 6,9-hemiketal 11,12-carbonate ester, there is obtained the epimers of 2'-propionyl-4''-deoxy-4''-amino-erythromycin A 6,9-hemiketal 11,12-carbonate ester and 2'-propionyl-4''-deoxy-4''-amino-erythromycin A 11,12-carbonate ester.

PREPARATION T

General Method—Alpha-alkoxy phenylacetic Acids

The appropriate benzene of formula XYC$_6$H$_4$ wherein X and Y are as defined herein is added to anhydrous chloral in a molar ratio of 4.24:1.00 and the mixture stirred and cooled to 0° C. Aluminum chloride (0.33 mole) is added portionwise to the mixture with vigorous stirring, the temperature being held to 0°–5° C. When addition of the aluminum chloride is complete, the reaction mixture is allowed to rise to a temperature of 15°–18° C. The mixture is stirred for one hour and then cooled to 0°–2° C. It is stirred at this temperature for an additional 60 hours and is then poured into an equal volume of ice water. The phenyl-trichloromethyl carbinol derivative is extracted with n-butyl acetate or n-butanol (2×250 ml.). The combined extract is washed with water (3×100 ml.) and is then dried over sodium sulfate. Removal of the solvent affords the carbinol which is purified by vacuum distillation if desired.

The carbinol is dissolved in the alcohol corresponding to the alkoxy group desired and is then added dropwise to a refluxing solution of the same alcohol containing at least 3 equivalents of KOH (based on the carbinol). The reaction mixture is refluxed for 3 hours following completion of addition and is then evaporated to dryness. The residue is taken up in water, the pH adjusted to 3.5, and the aqueous mixture extracted with an appropriate solvent (n-butyl acetate, ether, methylene chloride). The extract is washed with brine, followed by water and is then dried (Na$_2$SO$_4$) and evaporated to dryness to give the product.

What is claimed is:

1. A compound having the formula

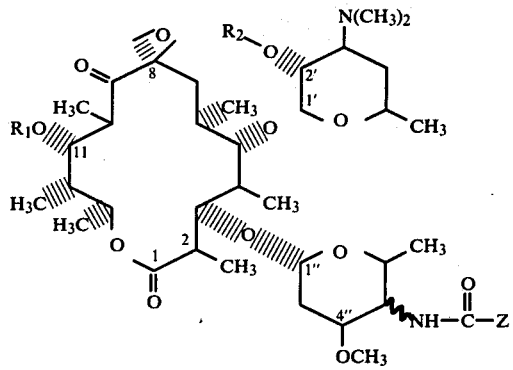

wherein each of $R_1$ and $R_2$ is selected from the group consisting of hydrogen and alkanoyl having from two to three carbon atoms;
Z is selected from the group consisting of
(a) $-(CH_2)_m-C(CH_3)_3$, (b) 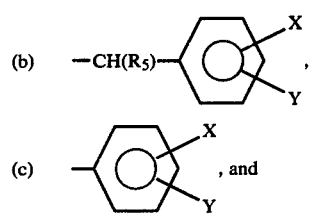

(c) (structure), and (d) $-(CH_2)_m$-heterocyclyl;
m is 0 or 1;
$R_5$ is selected from the group consisting of hydrogen, chloro, hydroxy, methyl, amino and alkoxy having from one to four carbon atoms;
X is selected from the group consisting of hydrogen, chloro, bromo, fluoro, alkyl having from one to four carbon atoms, alkoxy having from one to four carbon atoms;
Y is selected from the group consisting of X, trifluoromethyl and carbalkoxy having from two to five carbon atoms;
heterocyclyl is selected from the group consisting of thienyl, pyrazinyl, pyridyl, furyl, imidazolyl, thiazolyl, isothiazolyl, oxazolyl, isoxazolyl, pyrrolyl, thiadiazolyl and monomethyl derivatives of said heterocyclyls;
and the pharmaceutically acceptable acid addition salts thereof.

2. A compound according to claim 1 wherein Z is

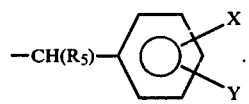

3. A compound according to claim 2 wherein X is hydrogen.

4. A compound according to claim 3 wherein $R_5$ is alkoxy.

5. A compound according to claim 4 wherein $R_5$ is methoxy and $R_2$ is hydrogen.

6. The compound according to claim 5 wherein Y is hydrogen and $R_1$ is acetyl.

7. A compound according to claim 2 wherein $R_5$ is chloro.

8. A compound according to claim 7 wherein each of X and $R_2$ is hydrogen.

9. The compound according to claim 8 wherein Y is hydrogen and $R_1$ is acetyl.

10. A compound according to claim 2 wherein each of $R_5$ and X is hydrogen.

11. The compound according to claim 10 wherein Y is fluoro, and each of $R_1$ and $R_2$ is hydrogen.

12. A compound according to claim 10 wherein Y is methoxy and $R_1$ is acetyl.

13. The compound according to claim 10 wherein each of $R_1$, $R_2$ and Y is hydrogen.

14. The compound according to claim 1 wherein Z is $-C(CH_3)_3$; $R_2$ is hydrogen and $R_1$ is acetyl.

15. A compound according to claim 2 wherein $R_5$ is amino and each of X and Y is hydrogen.

16. A compound according to claim 1 wherein Z is

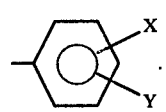

17. A compound according to claim 16 wherein X is hydrogen.

18. A compound according to claim 17 wherein Y is fluoro and $R_2$ is hydrogen.

19. A compound according to claim 18 wherein Y is 2-fluoro.

20. A compound according to claim 17 wherein Y is alkoxy.

21. A compound according to claim 1 wherein Z is $-(CH_2)_m$-heterocyclyl.

22. A compound according to claim 21 wherein m is 0 and each of $R_1$ and $R_2$ is hydrogen.

23. The compound according to claim 22 wherein heterocyclyl is 3-isoxazolyl, said compound being 4″-deoxy-4″-(3-isoxazolyl)carboxamido-oleandomycin.

24. The compound according to claim 22 wherein heterocyclyl is 4-methyl-5-oxazolyl, said compound being 4″-deoxy-4″-(4-methyl-5-oxazolyl)carboxamido-oleandomycin.

25. The compound according to claim 22 wherein heterocyclyl is 4-methyl-5-thiazolyl, said compound being 4″-deoxy-4″-(4-methyl-5-thiazolyl)carboxamido-oleandomycin.

26. The compound according to claim 22 wherein heterocyclyl is 2-pyrazinyl, said compound being 4″-deoxy-4″-(2-pyrazinyl)carboxamido-oleandomycin.

27. A compound selected from the group consisting of those having the formulae

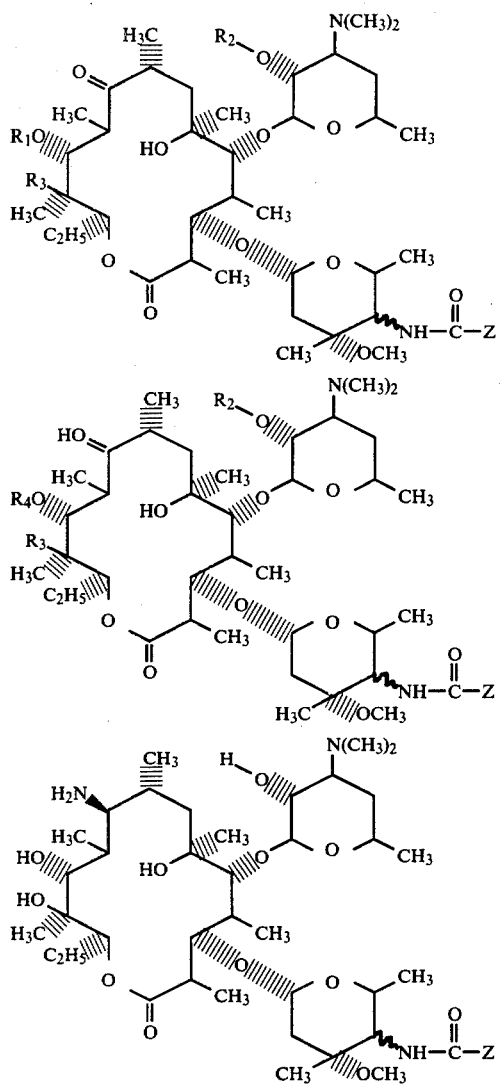

wherein each of $R_1$ and $R_2$ is selected from the group consisting of hydrogen and alkanoyl having from two to three carbon atoms; $R_3$ is selected from the group consisting of hydrogen and hydroxy; $R_4$ is alkanoyl having from two to three carbon atoms; $R_4O$ and $R_3$ when taken together are

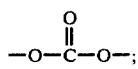

$R_1O$ and $R_3$ when taken together are

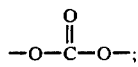

Z is selected from the group consisting of
(a) $(CH_2)_m-C(CH_3)_3$, (b) $-CH(R_5)-\phantom{X}\begin{array}{c}X\\ \\Y\end{array}$, (c) $-\phantom{X}\begin{array}{c}X\\ \\Y\end{array}$, and (d) $(CH_2)_m$-heterocyclyl;

m is 0 or 1;

$R_5$ is selected from the group consisting of hydrogen, chloro, hydroxy, methyl, amino and alkoxy having from one to four carbon atoms;

X is selected from the group consisting of hydrogen, chloro, bromo, fluoro, alkyl having from one to four carbon atoms, alkoxy having from one to four carbon atoms;

Y is selected from the group consisting of X and trifluoromethyl; and heterocyclyl is selected from the group consisting of thienyl, pyridyl, pyrazinyl, furyl, imidazolyl, thiazolyl, isothiazolyl, oxazolyl, isoxazolyl, pyrrolyl, thiadiazolyl, and monomethyl derivatives of said heterocyclyls;

and the pharmaceutically acceptable acid addition salts thereof.

28. A compound according to claim 27 wherein Z is $-C(CH_3)_3$.

29. A compound according to claim 27, formula II, wherein $R_3$ is hydroxy.

30. A compound according to claim 29 wherein Z is $-CH(R_5)-\phantom{X}\begin{array}{c}X\\ \\Y\end{array}$.

31. A compound according to claim 30 wherein each of X and $R_5$ is hydrogen.

32. The compound according to claim 31 wherein each of Y, $R_1$ and $R_2$ is hydrogen.

33. The compound according to claim 31 wherein Y is 2-fluoro, and each of $R_1$ and $R_2$ is hydrogen.

34. A compound according to claim 30 wherein $R_5$ is chloro and X is hydrogen.

35. A compound according to claim 30 wherein $R_5$ is alkoxy and X is hydrogen.

36. A compound according to claim 30 wherein $R_5$ is amino and X is hydrogen.

37. A compound according to claim 27 wherein Z is $-(CH_2)_m$-heterocyclyl.

38. A compound according to claim 37 wherein m is 0.

39. A compound according to claim 38, formula II, wherein $R_3$ is hydroxy, and each of $R_1$ and $R_2$ is hydrogen.

40. The compound according to claim 39 wherein heterocyclyl is 3-isoxazolyl.

41. The compound according to claim 39 wherein heterocyclyl is 2-pyridyl.

* * * * *

UNITED STATES PATENT AND TRADEMARK OFFICE
CERTIFICATE OF CORRECTION

PATENT NO. : 4,180,654

DATED : DECEMBER 25, 1979

INVENTOR(S) : FRANK C. SCIAVOLINO

It is certified that error appears in the above-identified patent and that said Letters Patent are hereby corrected as shown below:

Col. 5, line 22, "aminoacrolide" should read -- aminomacrolide --.
Each of cols. 20 and 21, that portion of each formula reading

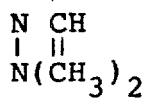   should read   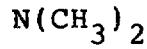

Each of cols. 20 and 21, that portion of each formula reading

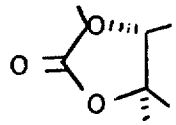   should read   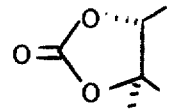

Each of cols. 23 and 25, that portion of each formula reading

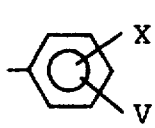   should read   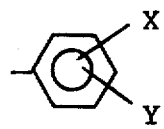

UNITED STATES PATENT AND TRADEMARK OFFICE
CERTIFICATE OF CORRECTION

PATENT NO. : 4,180,654  
DATED : December 25, 1979  
INVENTOR(S) : Frank C. Sciavolino It is certified that error appears in the above—identified patent and that said Letters Patent is hereby corrected as shown below:

Col. 27, delete that portion of the table comprising entries 11-17 and insert the following:

| $R_1O$        | $R_3$ | $R_2$ | $n$ | $R_5$ | $X$      | $Y$           | Method |
|---------------|-------|-------|-----|-------|----------|---------------|--------|
| $-O-C(O)-O-$  | Ac    | 1     | H   | H     | $3-CF_3$ |               | 1      |
| $-O-C(O)-O-$  | H     | 1     | H   | $3-OCH_3$ | $4-OCH_3$ |          | 1      |
| $-O-C(O)-O-$  | H     | 1     | H   | $3-Cl$ | $4-O-n-C_4H_9$ |       | 1      |
| $-O-C(O)-O-$  | Ac    | 1     | Cl  | H     | H        |               | 1      |
| $-O-C(O)-O-$  | H     | 1     | Cl  | H     | $2-OCH_3$ |              | 25     |
| $-O-C(O)-O-$  | H     | 1     | Cl  | $3-Cl$ | $4-CF_3$ |              | 1      |
| $-O-C(O)-O-$  | H     | 1     | Cl  | $3-OCH_3$ | $4-OH$ |              | 1      |

UNITED STATES PATENT AND TRADEMARK OFFICE
CERTIFICATE OF CORRECTION

PATENT NO : 4,180,654

DATED : December 25, 1979

INVENTOR(S) : Frank C. Sciavolino

It is certified that error appears in the above—identified patent and that said Letters Patent is hereby corrected as shown below:

Col. 47, claim 1, formula I, that portion of the formula reading

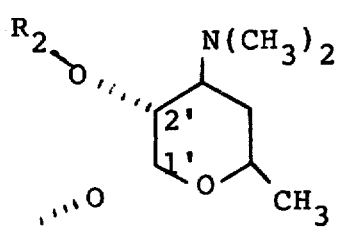 should read 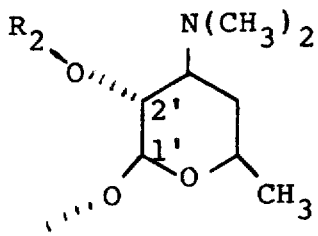

Signed and Sealed this

Fifteenth Day of April 1980

[SEAL]

Attest:

SIDNEY A. DIAMOND

Attesting Officer

Commissioner of Patents and Trademarks